United States Patent [19]
Herzinger et al.

[11] Patent Number: 6,084,675
[45] Date of Patent: Jul. 4, 2000

[54] ADJUSTABLE BEAM ALIGNMENT COMPENSATOR/RETARDER WITH APPLICATION IN SPECTROSCOPIC ELLIPSOMETER AND POLARIMETER SYSTEMS

[75] Inventors: Craig M. Herzinger; Blaine D. Johs, both of Lincoln, Nebr.

[73] Assignee: J. A. Woollam Co. Inc., Lincoln, Nebr.

[21] Appl. No.: 09/246,888

[22] Filed: Feb. 8, 1999

Related U.S. Application Data

[63] Continuation-in-part of application No. 08/530,892, Sep. 20, 1995, Pat. No. 5,666,201, which is a continuation-in-part of application No. 08/618,820, Mar. 20, 1996, Pat. No. 5,706,212, which is a continuation-in-part of application No. 08/997,311, Dec. 23, 1997, Pat. No. 5,946,098, which is a continuation-in-part of application No. 09/912,211, Aug. 15, 1997, Pat. No. 5,672,830.

[60] Provisional application No. 60/039,519, Mar. 3, 1997, provisional application No. 60/042,661, Apr. 4, 1997, and provisional application No. 60/045,966, Aug. 15, 1997.

[51] Int. Cl.$^7$ ........................................ G01J 4/00
[52] U.S. Cl. ............................. 356/369; 359/496
[58] Field of Search .................. 356/364, 365, 356/366, 367, 368, 369; 250/225; 359/487, 833, 834, 488, 599, 613, 614, 496, 497

[56] References Cited

U.S. PATENT DOCUMENTS

| | | |
|---|---|---|
| 0,548,495 | 10/1895 | Abbe . |
| 2,447,828 | 8/1948 | West . |
| 3,514,182 | 5/1970 | Banks ..................................... 359/833 |
| 3,817,624 | 6/1974 | Martin ..................................... 356/138 |
| 4,053,232 | 10/1977 | Dill et al. .............................. 356/118 |
| 4,556,292 | 12/1985 | Mathyssek et al. ................... 359/833 |
| 4,668,086 | 5/1987 | Redner ..................................... 356/33 |
| 5,016,980 | 5/1991 | Waldron ................................. 350/286 |
| 5,329,357 | 7/1994 | Bernoux et al. ........................ 356/369 |
| 5,373,359 | 12/1994 | Woollam et al. ....................... 356/328 |
| 5,475,525 | 12/1995 | Tournois et al. ....................... 359/245 |
| 5,504,582 | 4/1996 | Johs et al. .............................. 356/369 |
| 5,521,706 | 5/1996 | Green et al. ............................ 356/369 |
| 5,581,350 | 12/1996 | Chen et al. ............................. 356/369 |
| 5,596,406 | 1/1997 | Rosencwaig et al. .................. 356/327 |

OTHER PUBLICATIONS

Regression Calibration Method for Rotating Element Ellipsometers, Johs, Thin Film Solids, 234 (1993).
Data Analysis for Spectroscopic Ellipsometry, Jellison Jr., Thin Film Solids, 234 (1993).
Automated Rotating Element Ellipsometer: Calibration, Operation, & Peal Time Applications, Collins, Rev. Sci. Instrum. 61(8) (Aug. 1990).

*Primary Examiner*—Hoa Q. Pham
*Attorney, Agent, or Firm*—James D. Welch

[57] ABSTRACT

Disclosed is a compensator/retarder system which allows adjustment to eliminate introduction of significant deviation and/or displacement into the propagation direction of a beam of electromagnetic radiation caused to interact therewith, even when the present invention retarder system is caused to continuously rotate in a rotating compensator ellipsometer system. Also disclosed is a method of calibration of an ellipsometer/polarimeter system which includes a present invention compensator/retarder system.

13 Claims, 6 Drawing Sheets

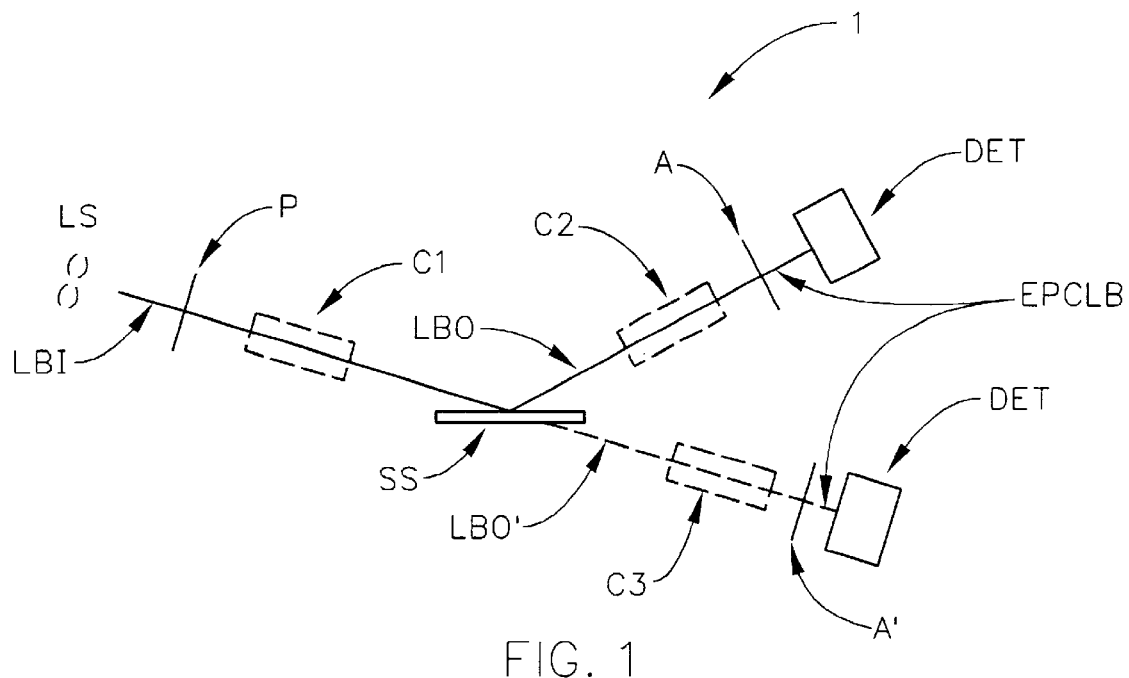
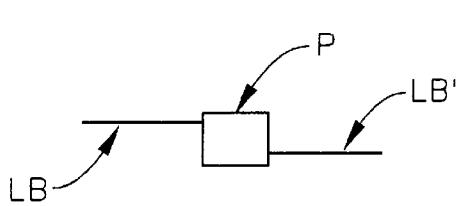
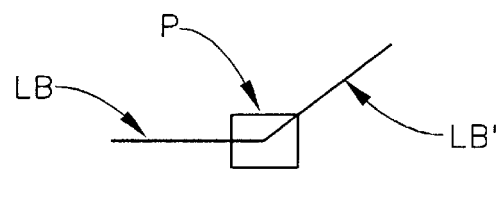
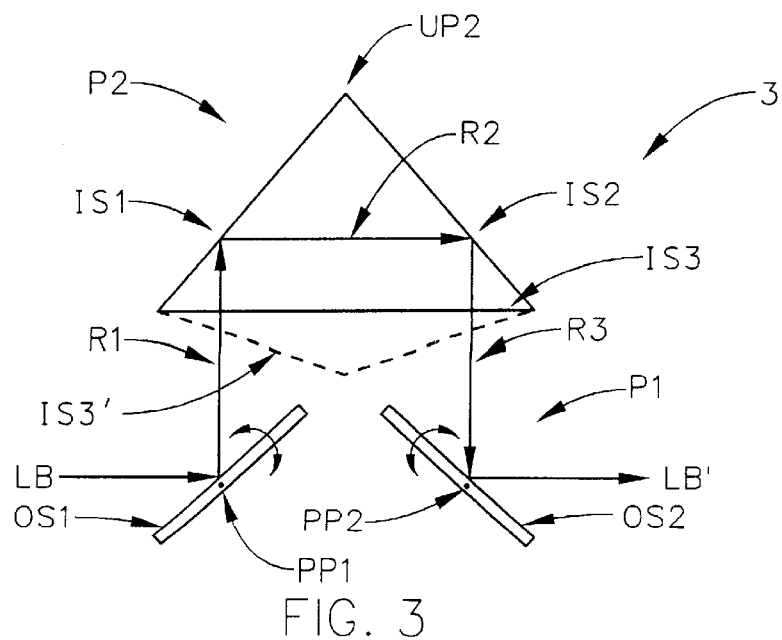

ADJUSTABLE BEAM ALIGNMENT COMPENSATOR/RETARDER WITH APPLICATION IN SPECTROSCOPIC ELLIPSOMETER AND POLARIMETER SYSTEMS

This Application is a CIP of application Ser. No. 08/530,892 filed Sept. 20, 1995, (now U.S. Pat. No. 5,666,201), and of application Ser. No. 08/618,820 filed Mar. 20, 1996, (now U.S. Pat. No. 5,706,212), and of application Ser. No. 08/997,311 filed Dec. 23, 1997, now U.S. Pat. No. 5,946,098. This Application is further a CIP of application Ser. No. 08/912,211, filed Aug. 15, 1997, now U.S. Pat. No. 5,872,630 which depends from the 210 and 212 Patents and is further a CIP of Provisional Applications Ser. Nos. 60/039,519 filed Mar. 3, 1997, and 60/042,661 filed Apr. 4, 1997 and 60/045,966 filed Aug. 15, 1997.

TECHNICAL FIELD

The present invention relates to ellipsometer/polarimeter systems, and more particularly to a compensator/retarder system which provides adjustment to eliminate introduction of significant deviation and/or displacement into the propagation direction of a beam of electromagnetic radiation caused to interact therewith, even when, for instance, a present invention compensator/retarder system is caused to continuously rotate in a rotating compensator ellipsometer system. As well, the present invention provides a method of calibration of an ellipsometer/polarimeter system which comprises a present invention compensator/retarder system that is continuously rotated in use.

BACKGROUND

Polarimeters and ellipsometers are comprised of optical elements such as polarizer and retarder systems. Polarimeter systems allow the polarization state of a polarized beam of electromagnetic radiation to be determined, and ellipsometer systems allow detection of change in polarization state of a polarized beam of electromagnetic radiation resulting from interaction with a sample system to be determined, said change in polarization state being associated with optical and physical properties of said sample system. For general information it is noted that the polarization state of a polarized beam of electromagnetic radiation is determined by:

a. ratio of orthogonal components, (related to PSI);
b. phase angle between said orthogonal components, (related to DELTA);
c. absolute value of one orthogonal component; and
d. the direction of rotation, or handedness.

It is noted that an ideal polarizer would pass only linearly polarized electromagnetic radiation aligned with the fast axis thereof, and would reject all electromagnetic radiation in an orthogonal orientation. That is, the extinction ration would be essentially infinite. The Mueller Matrix for an ideal polarizer is provided below:

$$\text{POLARIZER IDEAL} = \begin{bmatrix} 1 & 1 & 0 & 0 \\ 1 & 1 & 0 & 0 \\ 0 & 0 & 0 & 0 \\ 0 & 0 & 0 & 0 \end{bmatrix}$$

An ideal Retarder system would enter a phase retardation between orthogonal components of polarized electromagnetic radiation without preferentially modifying the intensity of either orthogonal component thereof. The Mueller Matrix of an ideal Retarder is:

$$\text{RETARDER IDEAL} = \begin{bmatrix} 1 & 0 & 0 & 0 \\ 0 & 1 & 0 & 0 \\ 0 & 0 & \cos(r) & \sin(r) \\ 0 & 0 & -\sin(r) & \cos(r) \end{bmatrix}$$

where "r" is the entered retardence.

As even very good compensator/retarder systems tend to preferentially modify one orthogonal component of an electromagnetic beam of radiation, (including those presented in this Disclosure), it is necessary to modify said Mueller Matrix to account for said effect. The Mueller Matrix of a Retarder system which accounts for preferential modification of one orthogonal component of a polarized beam of electromagnetic radiation is:

RETARDER LESS IDEAL =

$$\begin{bmatrix} 1 & -\cos(2\psi) & 0 & 0 \\ -\cos(2\psi) & 1 & 0 & 0 \\ 0 & 0 & \sin(2\psi)\cos(r) & \sin(2\psi)\sin(r) \\ 0 & 0 & -\sin(2\psi)\sin(r) & \sin(2\psi)\cos(r) \end{bmatrix}$$

where "r" is again the retardence entered. Note that where Retarder system PSI ($\Psi$) is forty-five (45) degrees, said Mueller Matrix reduces to the ideal Mueller Matrix.

It is additionally noted that the value of "r" should be in a range where an ellipsometer system in which it is a component is not severely sensitive to changes therein as, for instance, a function of wavelength. In Rotating Compensator Ellipsometers, it is disclosed that a value of "r" between ninety (90) and one-hundred-fifty (150) degrees is generally acceptable. It is also noted that typical off-the-shelf Retarder systems often exhibit an "r" with a (1/wavelength) response such that "r" values are not within said 90 to 150 degree range, when observed over a wavelength range of say, two-hundred-fifty (250) to one-thousand (1000) nm.

It is a requirement of an ideal optical element that a beam of electromagnetic radiation caused to interact therewith not have its direction of propagation deviated or displaced thereby. This is especially critical where an optical element must be rotated in use.

It is further desirable that an optical element not exhibit sensitivity of, for instance, extinction ratio, or retardence entered between orthogonal components of an electromagnetic beam of radiation caused to interact therewith, as a function of beam alignment with respect thereto.

As well, it is desirable that optical elements be easy to fabricate and that fabrication be from easily obtainable materials.

Continuing, the practice of ellipsometry requires that data reflecting change in polarization state of an electromagnetic beam of radiation resulting from interaction with a sample system be obtained and that said data be compared to data generated by use of a proposed mathematical model. Said mathematical model must take into account all nonidealities of optical elements present in the ellipsometer utilized. It is thus preferable to have as few nonidealities present in optical elements as is possible, in order to simplify mathematical model complexity.

With an eye to the present invention, a Search of Patents was conducted. Said Search was focused on polarizers, and on compensator/retarder systems which might provide relatively stable retardation over a range of wavelengths without imposing deviation or displacement in a beam of electromagnetic radiation caused to pass therethrough.

Regarding compensator/retarder systems, Patents were found which show elements with geometry somehow similar to geometry of the present invention compensator/retarder systems, but the present invention use was not found. In particular, attention is directed to the Figure in U.S. Pat. No. 548,495 to Abbe; FIG. 2 in U.S. Pat. No. 4,556,292 to Mathyssek et al.; FIGS. 1 & 4 in U.S. Pat. No. 5,475,525 Tournois et al.; and FIG. 10 in U.S. Pat. No. 5,016,980 Waldron. U.S. Pat. No. 3,817,624 to Martin and U.S. Pat. No. 2,447,828 to West were also identified.

Additional searching of Patents identified Dill U.S. Pat. No. 4,053,232 which describes a Rotating-Compensator Ellipsometer System, which operates utilizes monochromatic light. Two Patents which identify systems which utilize Polychromatic light in investigation of material systems are described in U.S. Pat. Nos. 5,596,406 and 4,668,086, to Rosencwaig et al. and Redner, respectively, were also identified. Also identified Woollam et al, U.S. Pat. No. 5,373,359 as it describes a Rotating Analyzer Ellipsometer System which utilizes white light. Patents continued from the 359 Woollam et al. U.S. Pat. Nos. 5,504,582 to Johs et al. and 5,521,706 to Green et al. Said 582 Johs et al. and 706 Green et al. Patents describe use of polychromatic light in a Rotating Analyzer Ellipsometer System. Bernoux et al., U.S. Pat. No. 5,329,357 is identified as it describes an ellipsometer system in which polarizer rotation is caused during use. Chen et al., U.S. Pat. No. 5,581,350 is identified as it describes the application of regression in calibration of ellipsometer systems. An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration. An article by Jellison Jr. titled "Data Analysis for Spectroscopic Ellipsometry", Thin Film Solids, 234, (1993) is idnetified as it describes a method of determining the accuracy with which certain data points can be measured, which information allows adding a weighting factor to a curve fitting regression procedure as applied to a multiplicity of data points, said weighting factor serving to emphasize the effect of more accurate and precise data. A book by Azzam and Bashara titled "Ellipsometry and Polarized light" North-Holland, 1977 is disclosed and incorporated herein by reference for general theory. An article by Collins titled "Automated Rotating Element Ellipsometers: Calibration, Operation, and Real-Time Applications", Rev. Sci. Instrum. 61(8), August 1990 is identified as it provides insight into rotating element ellipsometers. An article by Kleim et al. titled "Systematic Errors in Rotating-Compensator Ellipsometry" published in J. Opt. Soc. Am./ Vol. 11, No. 9, September 1994 is identified as it describes calibration of rotating compensator ellipsometers. An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof. Also disclosed are articles by Schubert et al. which describe "Generalized Ellipsometry". The first thereof is titled "Extension Of Rotating-Analyzer Ellipsometry To Generalized Ellipsometry: Determination Of The Dielectric Function Tensor From Uniaxial TiO2", J. Opt. Soc. Am. A. 13, (1996). The second such article is authored by M. Schubert alone and is titled "Polarization Dependent Parameters Of Arbitrary Anisotropic Homogeneous Epitaxial Systems", Phys. Rev. B 53, (1996). The third such article is titled "Generalized Transmission Ellipsometry For Twisted Biaxial Dielectric Media: Application To Chiral Liquid Crystals", J. Opt. Soc. Am. A/Vol. 13, No. 9 (1996). Further identified for authority regarding regression is a book titled Numerical Recipes in "C", 1988, Cambridge University Press.

A compensator/retarder system which can be configured so that it introduces essentially no deviation or displacement into a beam of electromagentic radiation caused to interact therewith, it should then be appreciated, would provide utility. The present invention provides an optical compensator/retarder system which demonstrates acceptably ideal behavior over relatively large wavelength ranges, and which can be applied to usage in rotating compensator ellipsometer systems.

DISCLOSURE OF THE INVENTION

The present invention system is a compensator/retarder system comprising, as viewed in upright side elevation, first and second orientation adjustable mirrored elements which each have reflective surfaces. Said compensator/retarder system further comprises a third element which, as viewed in upright side elevation, presents with first and second sides which project to the left and right and downward from an upper point and said third element is made of material which provides reflective interfaces on first and second sides inside thereof. Said third element is oriented, with respect to said first and second orientation adjustable mirrored elements, such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation. This is the case even when said compensator/retarder is caused to rotate about the propagation direction locus of said beam of essentially horizontally oriented electromagnetic radiation. The result of use of said compensator/retarder is that retardation is entered between orthogonal components of said input electromagnetic beam of radiation.

Said compensator/retarder system can also comprises means for imparting at least one of:

translational; and rotational;

motion, in at least one dimension, to at least one of said first and second orientation adjustable mirrored elements.

It is noted that said translational motion of said at least one of said first and second orientation adjustable mirrored elements can be in any X-Y-Z direction, and rotational motion thereof can be likewise be in three dimensions, as can be enabled by a ball-joint type means. However, as said first and second orientation adjustable mirrored elements have a depth dimension, translational motion in a depth oriented direction is typically unnecessary.

A primary application of the present invention compensator/retarder is in spectroscopic ellipsometer/polarimeter systems which comprise, in sequence:

a source of electromagnetic radiation;
a polarizer system;
a compensator/retarder;
an analyzer; and
a detector system.

A method of practicing ellipsometry/polarimetry comprises the steps of:

a. providing a spectroscopic ellipsometer/polarimeter system sequentially comprising:
   a source of electromagnetic radiation;
   a polarizer;
   a present invention compensator/retarder system as described infra herein;
   an analyzer system; and
   a detector system;
b. placing a sample system into said spectroscopic ellipsometer/polarimeter system;
c. causing said source of electromagnetic radiation to provide a beam of electromagnetic radiation to said sample system; and
d. detecting said beam of electromagentic radiation after interaction thereof with said sample system.

Said method of practicing ellipsometry/polarimetry can further comprise the step of causing said compensator/retarder system to rotate during use about the propagation direction locus of said input beam of essentially horizontally oriented electromagnetic radiation.

Said method of practicing ellipsometry/polarimetry can further comprise the step of adjusting the orientation of said first and second orientation adjustable mirrored elements so that an electromagentic beam which is caused to exit from said compensator/retarder system is undeviated and undisplaced from the locus of said input beam of electromagnetic radiation, even when said compensator/retarder system is caused to rotate.

Said method of practicing ellipsometry/polarimetry can further include the step of changing the orientation of said spectroscopic ellipsometer/polarimeter system so that a beam of electromagentic radiation entered thereto is not oriented horizontally with respect to an external frame of reference, but so that relative relationships between said first and second orientation adjustable mirrored elements and said third element are maintained.

And said method of practicing ellipsometry/polarimetry can further comprise the step of causing said compensator/retarder system to rotate during use about the propagation direction locus of said input beam of electromagnetic radiation which is no longer oriented horizontally with respect to said external frame of reference.

An alternative description of a present invention compensator/retarder system provides for first and second orientation adjustable mirrored elements which each have reflective surfaces. Said compensator/retarder system further comprises a third element which presents with first and second sides which project at an angle with respect to one another from a common point and said third element is made of material which provides reflective interfaces on first and second sides inside thereof. Said third element is oriented with respect to said first and second orientation adjustable mirrored elements such that in use an input electromagnetic beam of radiation caused to approach one of said first and second orientation adjustable mirrored elements, is caused to externally reflect therefrom and enter said third element and essentially totally internally reflect from one of said first and second sides thereof, then essentially totally internally reflect from the other of said first and second sides and then proceed to and reflect from the other of said first and second orientation adjustable mirrored elements and proceed along a propagation direction locus which is essentially undeviated and undisplaced from that of said input electromagentic beam of radiation, even when said compensator/retarder is caused to rotate; with a result being that retardation is entered between orthogonal components of said input electromagnetic beam of radiation.

And again, said compensator/retarder system can further comprise means for imparting at least one of:
   translational; and
   rotational;
motion, in at least one dimension, to at least one of said first and second orientation adjustable mirrored elements. And said compensator/retarder system can further comprise means for causing said compensator/retarder system to rotate during use about the propagation direction locus of said input beam of electromagnetic radiation.

Continuing, to provide insight to a particularly relevent application of the present invention compensator/retarder system, it is noted that it is generally considered that while Rotating Compensator Material System Investigation Systems, (eg. Rotating Compensator Ellipsometers), provide many benefits, (eg. Material System PSI and DELTA investigation limiting "dead-spots" are not present), that in the absence of essentially Achromatic "ideal" Compensators it would be prohibitively difficult and expensive to build, calibrate and utilize a "Spectroscopic" Rotating Compensator Material System Investigating System. This is to be understood in light of the fact that Compensators which are essentially Achromatic, (ie. provide essentially constant retardation over a large range of Wavelengths, such as 190–1000 nanometers), are not generally and economically available as off-the-shelf items.

The present invention compensator/retarder system can be, however, applied in an affordable, easy to calibrate and utilize present invention Spectroscopic Rotating Compensator Material System Investigation System comprising a Source of a Polychromatic Beam of Electromagnetic Radiation, a Polarizer, a Stage for Supporting a Material System, an Analyzer, a Dispersive Optics and at least one Photo Array Detector Element System which contains a multiplicity of Detector Elements, which Spectroscopic Rotating Compensator Material System Investigation System further comprises at least one Compensator(s) positioned at a location selected from the group consisting of: (before said stage for supporting a sample system and after said stage for supporting a sample system and both before and after said stage for supporting a sample system).

While it is known that generally available Compensators do not provide an exact Ninety (90) Degrees of Retardation at all wavelengths over a relatively large range of Wavelengths, the present invention, as described supra herein, utilizes a Regression based Calibration procedure which compensates for said non-ideal Compensator Retardation characteristics. And while it is true that the sensitivity and accuracy of a Rotating Compensator Material System Investigation System degrades as the Retardance provided by a utilized Compensator approaches zero (0.0) or one-hundred-eighty (180) degrees, it has been found that Compensators which demonstrate Retardation, over a range of utilized Wavelengths, of from forty (40) to one-hundredseventy (170) degrees, are acceptable for use in the present invention, and allow achieving very impressive results over a demonstrated relatively large range of wavelengths, (eg. at least two-hundred-fifty (250) to one-thousand (1000) nanometers).

When the present invention Spectroscopic Rotating Compensator Material System Investigation System is used to investigate a Material System present on said Stage for Supporting a Material System, said Analyzer and Polarizer are maintained essentially fixed in position and at least one of said at least one Compensator(s) is/are caused to continuously rotate while a Polychromatic Beam of Electromagnetic Radiation produced by said Source of a Polychromatic Beam of Electromagnetic Radiation is caused to pass through said Polarizer and said Compensator(s). Said Polychromatic Beam of Electromagnetic Radiation is also caused to interact with said Material System, pass through said Analyzer and interact with said Dispersive Optics such that a Multiplicity of Essentially Single Wavelengths are caused to simultaneously enter a corresponding multiplicity of Detector Elements in said Detector System Photo Array.

A method of calibrating a present invention Spectroscopic Rotating Compensator Material System Investigation System can comprise the steps of:

a. providing a present invention Spectroscopic Rotating Compensator Material System Investigation System as just described infra herein.

b. developing a Mathematical Model of said Spectroscopic Rotating Compensator Material System Investigation System which comprises as Calibration Parameter variables Polarizer Azimuthal Angle Orientation, present Material System PSI, present Material System DELTA, Compensator Azimuthal Angle Orientation(s), Matrix Components of said Compensator(s), Analyzer Azimuthal Angle Orientation, and optionally Detector Element Image Persistance and Readout non-idealities, which Mathematical Model is effectively a Transfer Function which enables calculation of Electromagnetic Beam Intensity as a function of Wavelength detected by a Detector Element, given Intensity as a function of wavelength provided by said Source of a Polychromatic Beam of Electromagnetic Radiation, said Mathematical Model optionally providing equations for Coefficients of Terms in said Transfer Function, said Coefficients of terms being functions of Calibration Parameters;

c. causing a Polychromatic Beam of Electromagnetic Radiation produced by said Source of a Polychromatic Beam of Electromagnetic Radiation, to pass through said Polarizer, interact with a Material System caused to be in the path thereof, pass through said Analyzer, and interact with said Dispersive Optics such that a Multiplicity of Essentially Single Wavelengths are caused to simultaneously enter a corresponding Multiplicity of Detector Elements in said at least one Detector System, with said Polychromatic Beam of Electromagnetic Radiation also being caused to pass through said Compensator(s) positioned at a location selected from the group consisting of: (before said Stage for Supporting a Material System and after said Stage for Supporting a Material system and both before and after said Stage for Supporting a Sample System);

d. obtaining an at least Two Dimensional Data Set of Intensity Values vs. Wavelength and a parameter selected from the group consisting of: (Angle-Of-Incidence of said Polychromatic Beam of Electromagnetic Radiation with respect to a present Material System, and Azimuthal Angle Rotation of one element selected from the group consisting of: (said Polarizer and said Analyzer)), over time, while at least one of said at least one Compensator(s) is caused to continuously rotate and, optionally, from said data set calculating numerical values for Coefficients of Terms in the Transfer Function for said Spectroscopic Rotating Compensator Material System Investigation System;

e. performing a Mathematical Regression of said Mathematical Model onto said at least Two Dimensional Data Set and/or onto values for Coefficients of Terms in the Transfer Function to evaluate said Calibration Parameters;

said Regression based Calibration Procedure evaluated Calibration Parameters serving to compensate said Mathematical Model for non-Achromatic characteristics and non-Idealities of said Compensator(s), and for Azimuthal Angle Orientations of said Polarizer, Analyzer and Compensator(s).

In addition, evaluation of Detector System Detector Element Image Persistance and Readout non-Ideality compensation Calibration Parameters also included in the Mathematical Model, can simultaneously be carried out in the Mathematical Regression Procedure.

It is noted that where two Compensators are present, each can be rotated at essentially the same, or different speeds.

Said Method of Calibrating a Spectroscopic Rotating Compensator Material System Investigation System can also include, in the step of providing a Mathematical Model, the steps of providing a Matrix Representation of each of said Polarizer, present Material System, said Compensator(s), and said Analyzer, and determining a Mathematical Transfer Function relating Electromagnetic Beam Intensity Out to Intensity In, as a function of Wavelength, by multiplication of said Matrices in a Spectroscopic Rotating Compensator Material System Investigation System element presence representing order.

Said Method of Calibrating a Spectroscopic Rotating Compensator Material System Investigation System can involve, in the step of calculating values of Coefficients of a Transfer Function from said Data Set, the calculation of values of Coefficients of a Fourier Series, (eg. $\alpha_2$, $\alpha_4$, $\beta_2$, $\beta_4$, in Eqs. 11–14 supra).

Additionally, said Method of Calibrating a Spectroscopic Rotating Compensator Material System Investigation system can further comprise the step of Parameterizing Calibration Parameters by representing variation as a function of Wavelength, (or perhaps Angle-Of-Incidence of said Polychromatic Beam of Electromagnetic Radiation with respect to a Surface of an Investigated Material System or Other Variable), by a Calibration Parameter containing Mathematical Equation, Calibration Parameter(s) in said Calibration Parameter containing Mathematical Equation being evaluated during said Mathematical Regression. (See Eqs. 51 & 52 supra). When this is done the Calibration Parameter containing Mathematical Equation provides a functional relationship, and, it is noted, can even be a constant value over a range of, for instance, Wavelenghts, (eg. Polarizer Azimuthal Angle setting). (Note, said parametered approach to mathematical regression based calibration parameter evaluation is better described supra herein under the Headings GLOBAL REGRESSION MODES 1, 2 and 3).

It is further noted that the at least Two Dimensional Data Set can be obtained with the Spectroscopic Rotating Compensator Material System Investigation System oriented in a "Straight-Through" or "Material-System-Present" configuration. In the first configuration open atmosphere essentially constitutes a material system, and a Polarized Electromagnetic Beam passes directly through the Polarizer, Compensator(s) and Analyzer into the Detector System. In the second configuration a Material System is present which presents PSI and DELTA values other than those of the open atmosphere so that a Polychromatic Electromagnetic Beam passes through the Polarizer, possibly a Compensator, and then interacts with a Material System, before passing through, possibly, a Compensator, an Analyzer and into the Detector System. Compensator(s), it should be understood, can be present before and/or after the Material System.

With the above general description of the present invention System and Calibration Method in mind, attention is directed to providing a detailed demonstration of the Calibration Procedure of the present invention as applied to a Spectroscopic Rotating Compensator Ellipsometer System sequentially comprised of:

A Polychromatic Light Source
A Fixed Polarizer
A Material Sample
A Continuously Rotating Compensator
A Fixed AnalyzeR, and
A Detector Element containing Photo Array.

(Note: the Reflection mode side of FIG. 1 of this Disclosure shows this basic configuration where Compensator (C) is considered as removed and only Compensator (C') remains present).

It is to be appreciated, however, that the basic approach to calibration described directly, is adaptable for use in systems in which the Continuously Rotating Compensator is placed ahead of a Material System, and in systems in which two Compensators are present, one ahead of, and one after a Material System wherein one or both are caused to Continuously Rotate in use. For instance, in the case where a Rotating Compensator is placed ahead of the Material Sample, rather than thereafter, simply exchanging references to Polarizer and Analyzer in equations derived for the case where the Rotating Compensator is placed after the Material System, provides the applicable equations.

Transfer function equations for the Rotating Compensator system configured as recited above can be obtained from multiplication of Matrix Representations of the various components, in an appropriate order, in conjunction with Trig function containing Rotation Matrices, which serve to align coordinate systems between components. Eq. 1 shows said Matrix representation:

$$E(P, \Psi, \Delta, C, r1, r2, r3, r4, A) = \qquad (1)$$

$$\begin{pmatrix} 1 & 0 \\ 0 & 0 \end{pmatrix} \cdot \begin{pmatrix} \cos(A) & \sin(A) \\ -\sin(A) & \cos(A) \end{pmatrix} \cdot \begin{pmatrix} \cos(C) & -\sin(C) \\ \sin(C) & \cos(C) \end{pmatrix} \cdot \begin{pmatrix} r1 & r3 \\ r2 & r4 \end{pmatrix} \cdot$$

$$\begin{pmatrix} \cos(C) & \sin(C) \\ -\sin(C) & \cos(C) \end{pmatrix} \cdot \begin{pmatrix} \sin\Psi \cdot \sigma^{lk\Delta} & 0 \\ 0 & \cos\Psi \end{pmatrix} \cdot \begin{pmatrix} \cos(P) \\ \sin(P) \end{pmatrix}$$

where: $\Psi$ and $\Delta$ are the traditional ellipsometric parameters which describe the Material System;

P is the azimuthal orientation of the Polarizer;
C is the azimuthal orientation of the Rotating Compensator;
r1, r2, r3 & r4 are the Jones Matrix elements which describe the Compensator, (Note that a Jones Matrix is utilized, however, a Mueller Matrix or other Matrix could also be utilized);
A is the azimuthal orientation of the Analyzer.

The Light Intensity which is measured by a Detector is provided by multiplying through the Matrices in Eq. 1 to provide a Complex Result, then multiplying said Complex Result by its Complex Conjugate. Eq. 2 indicates this:

$$I(P,\Psi,\Delta,C,r1,r2,r3,r4,A) = E(P,\Psi,\Delta,C,r1,r2,r3,r4,A) \cdot E^*(P, \Psi,\Delta,C,r1,r2,r3,r4,A) \qquad (2)$$

The Intensity Equation I(t), (Eq. 8):

$$I(t) = I_0(DC + \alpha_2 \cos 2C + \beta_2 \sin 2C + \alpha_4 \cos 4C + \beta_4 \sin 4C) \qquad (8)$$

which results from said multiplication is very involved, but can be expressed in terms of intermediate results as provided in Eq. 3–7, via Eqs. 9.

$$p1 = \sin\Psi \cdot (\cos\Delta + i \cdot \sin\Delta) \cdot \cos P \qquad (3)$$
$$p2 = \cos\Psi \cdot \sin P$$

$$\begin{aligned} K1 &= (-p1 \cdot r3 + p2 \cdot r1) \\ K2 &= (p1 \cdot r1 + p2 \cdot r3) \\ K3 &= (-p1 \cdot r4 + p2 \cdot r2) \\ K4 &= (p1 \cdot r2 + p2 \cdot r4) \end{aligned} \qquad (4)$$

$$\begin{aligned} U1 &= (\cos(A) \cdot K2 + \sin(A) \cdot K4) \\ U2 &= (K3 + K2) \cdot \sin(A) + (K1 - K4) \cdot \cos(A) \\ U3 &= (\cos(A) \cdot K3 + \sin(A) \cdot K1) \end{aligned} \qquad (5)$$

$$V1 = U1 \cdot \overline{U1} \qquad V2 = U2 \cdot \overline{U2} \qquad V3 = U3 \cdot \overline{U3} \qquad (6)$$
$$V4 = 2 \cdot \text{Re}(U1 \cdot \overline{U2}) \quad V5 = 2 \cdot \text{Re}(U1 \cdot \overline{U3}) \quad V6 = 2 \cdot \text{Re}(U2 \cdot \overline{U3})$$

$$\begin{aligned} T1 &= V1 + V3 \quad T2 = V2 + V5 \quad T3 = V1 - V3 \\ T4 &= V4 + V6 \quad T5 = V4 - V6 \end{aligned} \qquad (7)$$

where Eqs. 9 provide that:

$$DC = \frac{3}{8} \cdot T1 + \frac{1}{8} \cdot T2 \qquad (9)$$

$$\alpha_2 = \frac{1}{2} \cdot T3 \quad \beta_2 = \frac{1}{4} \cdot T4$$

$$\alpha_4 = \frac{1}{8} \cdot (T1 - T2) \quad \beta_4 = \frac{1}{8} \cdot T5$$

and C=$\omega \cdot$t, where '$\omega$' is the angular frequency of the continuously rotating Compensator and I0 is an arbitrary constant.

(It is further noted that Eq. 8 is a truncated Fourier Series, and could include additional, higher harmonic terms).

Equations 1–9 are appropriate for a Material System which does not depolarize an Electromagnetic Beam used to investigate a Material System, such that Jones Matrix formalism is appropriate. If a Material System is investigated which does depolarize an investigation electromagnetic beam, then Mueller Matrix formalism can be substituted. As well, the "Isotropic" Material System Matrix in Eq. 1 could be replaced by a General Material System Matrix in the Rotating Compensator. This is described by M. Schubert in the context of "Generalized Ellipsometry", (see Background Section for citations to relevant articles which treat the topic of Generalized ellipsometry by Schubert).

If an ideal Compensator is assumed, where the Jones Matrix components are:

r1=1;
r2=0;
r3=0; and
r4=$e^{i-\delta}$;

then the Eqs. 9 become Eqs 10–14:

$$DC = (\tfrac{1}{2})(1+\cos\delta)[\cos 2A(\cos 2P - \cos 2\Psi) + \sin 2A \sin 2P \sin 2\Psi \cos\Delta] - \cos 2P \cos 2\Psi + 1 \quad (10)$$

$$\alpha_2 = -\sin 2A \sin 2P \sin\delta \sin 2\Psi \sin\Delta \quad (11)$$

$$\beta_2 = \cos 2A \sin 2P \sin\delta \sin 2\Psi \sin\Delta \quad (12)$$

$$\alpha_4 = (\tfrac{1}{2})(1-\cos\delta)[\cos 2A(\cos 2P - \cos 2\Psi) - \sin 2A \sin 2P \sin 2\Psi \cos\Delta] \quad (13)$$

$$\beta_4 = (\tfrac{1}{2})(1-\cos\delta)[\sin 2A(\cos 2P - \cos 2\Psi) + \cos 2A \sin 2P \sin 2\Psi \cos\Delta] \quad (14)$$

It is noted that said Eqs. 10–14 are found in Kleim et al. as referenced in the Background Section of this Specification, with "A" and "P" interchanged. (The Kleim et al. work assumed a Rotating Compensator present prior to a Material System).

Continuing, Eqs. 10–14 are valid for an ideal Rotating Compensator System wherein the Azimuthal angles of the optics are perfectly aligned with the Material Sample frame of reference. In practice this is never true, and offset terms "A'", "P'" and "C'" must be entered to provide Eqs. 15a and 15b:

$$A = A' - A_s, \quad P = P' - P_2 \quad (15a)$$

$$C = C' - C_s \quad (15b)$$

where the A', C' and P' indicate dial readings and the As, Cs and Ps indicate Offset Angles to be determined by a Calibration Procedure.

Substituting Eq. 15b into Eq. 8 provides Eqs. 16a and 16b, and 17a and 17b for Fourier Coefficients, (note that the DC term is unchanged):

$$m\alpha_2 = \alpha_2 \cos 2C_5 - \beta_2 \sin 2C_5 \quad (16a)$$

$$m\beta_2 = \alpha_2 \sin 2C_5 + \beta_2 \cos 2C_5 \quad (16b)$$

$$m\alpha_4 = \alpha_4 \cos 4C_5 - \beta_4 \sin 4C_5 \quad (17a)$$

$$m\beta_4 = \alpha_4 \sin 4C_5 + \beta_4 \cos 4C_5 \quad (17b)$$

Continuing, the present invention simultaneously measures the Intensity of a multiplicity of essentially single wavelengths with a Photo Array, to determine Fourier Coefficients. And as the Diode Elements in the Photo Array are operated in a Charge Integration Mode, it is necessary to utilize a Hadamard analysis of the signal. In the preferred embodiment of the present invention, the Diode Array is synchronously read-out exactly sixteen (16) times during each rotation of the Rotating Compensator. The time varying signal, which results from modulation imposed by the Rotating Compensator, is given by Eq. 18. Eq. 19 represents a measured value at a given channel in a Photo Array for the i'th scan measured during the rotation.

$$s(t) = I_0 \cdot (DC + \alpha_2 \cos 2t + \beta_2 \sin 2t + \alpha_4 \cos 4t + \beta_4 \sin 4t) \quad (18)$$

$$h_i = \int_{(i-1)\cdot\frac{\pi}{8}}^{i\cdot\frac{\pi}{8}} s(t)\,dt \quad (19)$$

Substituting Eq. 18 into Eq. 19 and rearranging terms provides the following expressions, (Eqs. 20–24), for the Fourier Coefficients:

$$DC = \frac{\begin{array}{l} h_1 + h_2 + h_3 + h_4 + h_5 + h_6 + h_7 + h_8 + \\ h_9 + h_{10} + h_{11} + h_{12} + h_{13} + h_{14} + h_{15} + h_{16} \end{array}}{4 \cdot \pi \cdot I_0} \quad (20)$$

$$\alpha_2 = \frac{\begin{array}{l} h_1 + h_2 - h_3 - h_4 - h_5 - h_6 + h_7 + h_8 + \\ h_9 + h_{10} - h_{11} - h_{12} - h_{13} - h_{14} + h_{15} + h_{16} \end{array}}{8 \cdot I_0} \quad (21)$$

$$\beta_2 = \frac{\begin{array}{l} h_1 + h_2 + h_3 + h_4 - h_5 - h_6 - h_7 - h_8 + \\ h_9 + h_{10} + h_{11} + h_{12} - h_{13} - h_{14} - h_{15} - h_{16} \end{array}}{8 \cdot I_0} \quad (22)$$

$$\alpha_4 = \frac{\begin{array}{l} h_1 - h_2 - h_3 + h_4 + h_5 - h_6 - h_7 + h_8 + \\ h_9 - h_{10} - h_{11} + h_{12} + h_{13} - h_{14} - h_{15} + h_{16} \end{array}}{8 \cdot I_0} \quad (23)$$

$$\beta_4 = \frac{\begin{array}{l} h_1 + h_2 - h_3 - h_4 + h_5 + h_6 - h_7 - h_8 + \\ h_9 + h_{10} - h_{11} - h_{12} + h_{13} + h_{14} - h_{15} - h_{16} \end{array}}{8 \cdot I_0} \quad (24)$$

Equations 20–24 provide the means for extracting the Fourier Coefficients for the Rotating Compensator signal from the (hi) values which are measured by the Photo Array Diode Elements during continuous rotation of the Rotating Compensator.

It is emphasized that good quality electronics which employ the Video Integration Read-Out technique have been found to be very conducive to accurately measuring Fourier Coefficients using Photo Array Diode Elements. It is to be understood that said good quality electronics interface output signals from Photo Array Diode Elements to a computer system which collects and analyzes data. Preferred "Off-The-Shelf-Systems" which include good quality electronics, suitable for use in the present invention Rotating Compensator Material System Investigation System, are Zeiss Diode Array Spectrometer systems identified by manufacturer numbers selected from the group: MMS1 (300–1150 nm); UV/VIS MMS (190–230 nm); UV MMS (190–400 nm); AND IR MMS (900–2400 nm). Said Zeiss systems also include Dispersive Optics and Diode Element containing Photo Arrays. The Zeiss systems include twelve (12) bit dynamic range readout electronics, which provides a voltage pulse output. The present invention system provides additional good-quality electronics in the form of an integrator and Analog to Digital Converter. In use, the scanning rate of Diode Elements in a Zeiss system Photo Array is synchronized with the rotation of the Rotating Compensator of the present invention Rotating Compensator Material System Investigation System. Said synchronization is accomplished utilizing standard digital logic, and Diode Elements in the Photo Array are scanned sixteen (16) times during each rotation of the Rotating Compensator. It is further noted that the present invention preferably effects rotation of the Rotating Compensator with a hollow shaft Stepper Motor. A sequence of reference pulses is generated by a sensor attached to the Rotating Compensator, with said reference pulses being provided to good quality electronics simultaneous with the data provided by the Photo Array Diode Elements. Said reference pulses allow correlation of the angular position of the Rotating Compensator with data provided by the Photo Array Diode Elements.

Regarding Photo Array data, it is further noted that authors An and Collins describe some of the non-idealities which can be present when using a Photo Array Detector in a Spectroscopic Rotating Compensator Material System Investigation System. With the exception of the An and Collins correction for "Stray Light" (see An and Collins Eq.

13), however, none of the Photo Array non-ideality corrections which were presented in their paper were found necessary in implementing the preferred embodiment of the present invention. However, to allow a non-ideal Photo Array to be used in the present invention, the relevant corrections for a Image Persistence, and for Read Time in a Spectroscopic Rotating Compensator Material System Investigation System in which sixteen (16) Diode Element Scans are acquired for each Rotating Compensator revolution were derived, and are provided in Eqs. 25–34.

Image Persistence correction, where 'x' is the magnitude of the non-ideality:

$$ip\alpha_2 = \alpha_2 - 0.5 \cdot x \cdot [(2-\sqrt{2}) \cdot \alpha_2 + \sqrt{2} \cdot \beta_2] \quad (25)$$

$$ip\beta_2 = \beta_2 - 0.5 \cdot x \cdot [(2-\sqrt{2}) \cdot \beta_2 - \sqrt{2} \cdot \alpha_2] \quad (26)$$

$$ip\alpha_4 = \alpha_4 - x \cdot (\alpha_4 + \beta_4) \quad (27)$$

$$ip\beta_4 = \beta_4 - x \cdot (\beta_4 - \alpha_4) \quad (28)$$

$$ipDC = DC \quad (29)$$

Read Time correction, where 'p' is the channel read time of the diode array:

$$-c\alpha_2 = ip\alpha_2 - 0.5 \cdot \rho \cdot [(1+\sqrt{2}) \cdot ip\alpha_2 + ip\beta_2] \quad (30)$$

$$c\beta_2 = ip\beta_2 - 0.5 \cdot \rho \cdot [(1+\sqrt{2}) \cdot ip\beta_2 - ip\alpha_2] \quad (31)$$

$$c\alpha_4 = ip\alpha_4 - \rho \cdot (ip\alpha_4 + ip\beta_4) \quad (32)$$

$$c\beta_4 = ip\beta_4 + \rho \cdot (ip\alpha_4 - ip\beta_4) \quad (33)$$

$$cDC = \left(1 - \frac{4 \cdot \rho}{\pi}\right) \cdot ipDC \quad (34)$$

Eqs. 25–34 can be applied after Eqs. 10–17 to account for non-idealities in the Photo Array Diode Element readout. The Image Persistence and Read-Out non-ideality factors "x" and "p" can also be determined by defining them as Fit Parameters in a Calibration Regression procedure presented in the following section of this Specification.

For demonstration purposes, considering now the present invention Spectroscopic Rotating Compensator Material System Investigation System to be a Rotating Compensator Ellipsometer System with Diode Element Array read-out, it must be understood that to acquire usable data, Calibration must be performed. Said calibration provides numerical values for Azimuthal Orientation Off-set Angles of Polarizer, Analyzer and Compensator with respect to a Material System Frame of Reference, along with the Retardance of the Rotating Compensator as a function of Wavelength. In addition, Calibration Parameters to compensate non-idealities in Diode Elements in a Photo Array are calibrated.

The foundation of the Calibration Procedure was first announced in the 1993 paper by Johs, published in Thin Film Solids, cited in the Background Section herein. The same basic Calibration Procedure technique is further developed in Co-pending patent application Ser. No. 08/618,820 which describes calibration of a Rotating Compensator Ellipsometer System utilized in the Infra-red (IR) band of wavelengths. Both identified references, however, describe typical application of the Regression based Calibration technique to one (1) wavelength at a time. While this method does work, it can require two-hundred-fifty-six (256) sets of Calibration Parameters where a two-hundred-fifty-six (256) Diode Element Photo Array is utilized, with each Diode Element serving to monitor an essentially single wavelength. (Note, as the electromagnetic spectrum is continuous, an essentially single wavelength is to be understood to be a small range of wavelengths centered around some wavelength, which essentially single wavelength is intercepted by a Diode Element in a Photo Array).

In practice of the present invention a "Global" regression procedure is typically performed on a Two (2) Dimensional Data Set. Typically Polarizer Azimuthal Angle and Wavelength are selected as Data Set Independent variables, although electromagnetic beam Angle-of-Incidence with respect to a Material System surface could be selected as an Independent variable instead of, for instance, Wavelength or Polarizer Azimuthal Angle. It is also noted that the Regression based Calibration described in Co-pending application Ser. No. 08/618,820 required that two (2), at least two (2) Dimensional Data Sets be provided in each Regression procedure. The two Data Sets are obtained with different investigated Material System configurations being employed. For instance, Data Sets utilizing two different Material Systems, or one Material System present and a "Straight-through" configuration might be utilized. (Note, a "Straight-through" configuration results when no Material System is present, and an electromagnetic beam is caused to pass sequentially through a Polarizer, Compensator and Analyzer then enter a Photo Array Detector System, without interacting with a Material System) The present invention, in contrast, requires that only one Data Set be present. Said Data Set can be obtained with the Ellipsometer in Material System present or Straight-through configuration, although some benefits are realized when a Material System is utilized, (discussed supra herein). Of course, the present invention can be practiced utilizing two Data Sets.

As mentioned, the Regression based Calibration procedure of the present invention requires that an at least Two (2) Dimensional Data Set be experimentally obtained. Typically said Two (2) Dimensional Data Set has as Independent Variables, Polarizer, (where the Rotating Compensator is placed after a Material System), Azimuthal Angle, and Wavelength. Where a Rotating Compensator is placed before a Material System, an Analyzer Azimuthal Angle is utilized. As mentioned, Angle-of-Incidence of an investigation Electromagnetic Beam with respect to an investigated Material System surface can be substituted for an Analyzer or Polarizer Azimuthal Angle settings, but this is not preferred as Material System PSI and DELTA values vary therewith. Also, it is generally simpler to vary a Polarizer or Analyzer Azimuthal Angle in most Ellipsometer systems in practice. Continuing, data is simultaneously obtained from many Diode Elements, (which correspond to different Wavelengths), and subjected to the Hadamard analysis inherent in Eqs. 20–24, infra to provide Fourier Coefficients present in Eq. 18. (It is noted that a Photo Array can contain 256, 1024 or 2048 Diode Elements, and some thereof might provide a signal which of too small an intensity to be utilized. The present invention allows for utilizing only a user selected group of signals for this and other reasons).

It will be noted that Eqs. 8 and 18 contain a D.C. term "I0". This can be selected as a Fit Parameter in a Regression Procedure or a Normalization procedure can be implemented. Said Normalization can be with respect to the D.C. term, or a Normalizing Parameter can be included. The following Eqs 35a, 35b and 35c provide possible Normalizing Parameters:

$$\text{Norm} = \text{DC} \tag{35a}$$

$$\text{Norm} = \sqrt{(\alpha_2)^2 + (\beta_2)^2 + (\alpha_4)^2 + (\beta_4)^2 + (\text{DC})^2} \tag{35b}$$

or $$\text{Norm} = \sqrt{(\alpha_2)^2 + (\beta_2)^2 + (\alpha_4)^2 + (\beta_4)^2} \tag{35c}$$

Eq. 35a provides for Normalizing with respect to the D.C. term, Eq. 35b provides for Normalizing to a Parameter which depends on the D.C. Term and the Fourier Coefficients, while Eq. 35c provides for Normalizing to a Parameter which depends on Fourier Coefficients but not the D.C. Term. If Fourier Coefficients are not Normalized, (ie. the D.C. Term "IO" is not included as a Fit Parameter in a Calibration Parameter evaluating Regression Procedure, or Normalization is not performed), it should be appreciated that a "Floating" value result will be obtained for Calibration Parameters provided by application of the Calibration Parameter evaluating Regression onto said Fourier Series Coefficient values. As mentioned infra herein, the D.C. Component "IO" can be difficult to evaluate, often requiring a "Shutter" to block background light, dark current, readout electronics voltage offsets etc. As well, the D.C. component is more susceptible to instrumentation drift. As a result, use of Eq. 35c is preferred in the present invention Calibration Procedure to use of Eqs. 35a and 35b and to including "IO" in a Regression Procedure for evaluating Calibration Parameters. (Note that calibration data is taken with the Rotating Compensator Sample System Investigating System in a "Sample Present", rather than a "Straight Through" configuration, where such Eq. 35c normalization is practiced).

Normalized Fourier Coefficients can be then represented by Eqs 36–39:

$$n\alpha_2 = \frac{\alpha_2}{\text{Norm}} \tag{36}$$

$$n\beta_2 = \frac{\beta_2}{\text{Norm}} \tag{37}$$

$$n\alpha_4 = \frac{\alpha_4}{\text{Norm}} \tag{38}$$

$$n\beta_4 = \frac{\beta_4}{\text{Norm}} \tag{39}$$

A Global Calibration Data Set can be represented by Eq. 40:

$$MFD_{p,n} = \{(n\alpha_2)_{p,n}, (n\beta_2)_{p,n}, (n\alpha_4)_{p,n}, (n\beta_4)_{p,n}\} \tag{40}$$

where MFD stands for Measured Fourier Data, and where "P" is the Polarizer Angle and constitutes one Independent Variable, (and is typically varied within the range of from zero (0.0) to one-hundred-eighty (180) degrees, in ten (10) degree steps), and where "n" identifies the index of a selected Diode element, (channel), in the Photo Array, or alternatively stated, identifies a Second Independent Variable, (ie. Wavelength). It is noted that a typical system configuration would make use of Diode Elements (channels) 30–250 in a 256 channel Photo Array. The term "Global" emphasizes the presence of Wavelength Dependence. Utilizing the just described "P" range settings and Wavelength range, Eq. 41 indicates that the Global MFD Data Set would contain:

(180/10+1 polarizer settings)×(250−30+1 channels)×(4 Fourier components)=16,796 values  (41)

It is further noted that an approximate error in Fourier Data ( ), can be estimated from signal to noise at each Detector Channel, and subsequently used in the Regression Analysis of the Experimentally Obtained Data Set.

Continuing, use of Eqs. 3–17, 35–39 and (25–34 if Photo Array nonidealities are included), allows one to calculate, (ie. mathematically predict), values of Normalized Fourier Coefficients as in Eqs 36–39, which will be experimentally measured by a present invention Rotating Compensator Material System Investigation System. However, to make said mathematical prediction requires that Material System PSI and DELTA values be known, the Offset Angles $P_s$, $A_s$, and $C_s$ be known, and that Compensator Retardation '$\delta$' be known as well as any other Compensator non-idealities, and that the Photo Array nonidealities 'x' and '$\rho$' be known if necessary. Mathematically this can be represented by Eq. 42:

$$PFD_{p,n}(P, \Psi_n, \Delta_n, (P_s)_n, (C_s)_n, (A_s)_n, \delta_n, x_n, \rho_n) \tag{42}$$

Eq. 42 states that a Predicted Fourier Data (PFD) Set at a given Polarizer Azimuth and Photo Array Channel (Wavelength), is a function of identified variables, which variables constitute Calibration Parameters which must be provided numerical values. The present invention Regression procedure provides means for numerically evaluating the Calibration Parameters.

In all known prior art, separate Regression procedures have been carried out at each utilized Wavelength. If Two-Hundred (200) Wavelengths were utilized, then Two-Hundred (200) separate values for $P_s$, $A_s$ $C_s$ etc. would be obtained. The present invention Regression Procedure, however, teaches that Calibration Parameters as a function of an Independent Variable, (eg. Wavelength), can be "Parameterized". That is, a mathematical relationship requiring only a few (eg. perhaps two (2) or three (3) Parameters), can be generated to describe a functional relationship between the Calibration Parameter and the Independent Variable (eg. Wavelength), and the present invention Regression Procedure utilized to evaluate said Two (2) or Three (3) Parameters. For example, the Polarizer Azimuthal Offset ($P_s$) might be constant for all Wavelengths. Should this be the case then said Polarizer Azimuthal Offset ($P_s$) can be evaluated and stored, rather than, for instance, Two-Hundred (200) separate values at Two-Hundred (200) separate Wavelengths. In this instance, Eq. 43 indicates that a Global Calibration Parameter can be defined:

$$(P_s)_n = gP_s \tag{43}$$

In general, any of the discretely defined Calibration Parameters identified in Eq. 42, could be replaced by a Global Parametric Function as defined in Eq. 44:

$$CP_n = gCP(n, p_1, p_2, \ldots, p_k) \tag{44}$$

where $CP_n$ stands for any Calibration Parameter which is discretely defined for each "n"'th channel, (ie. the "n"'th Wavelength), and "gCP" is a global Parametric Function (as a function of an "n"'th channel number and "k" Calibration Parameters "pl . . . pk) which replace $CP_n$. A Parametric Function can be of any mathematical form, such as, but not limited to, polynomial, rational or trancendental (in the case of PSIn and DELTAn, a Parametric Function could be calculated from a multi-layer optical model for a Material System, using known Material Optical Constants and Parameterized Film Thicknesses). The important characteristic of a Parametric Function being that:

1. It accurately represents the behavior of the Calibration Parameter at each Independent Variable (eg. Photo Array Channel or Wavelength).
2. It accurately represents the behavior of the Calibration Parameter utilizing fewer Parameters than would be required to simply evaluate Calibration Parameters at each utilized Independent Variable (eg. Wavelength).

In terms of Eq. 44 this can be stated that "k" (the number of Calibration Parameters), is less than "n" (the number of channels).

It is to be understood that preferred Global Parameter Function form utilized in the present invention depends upon the particular embodiment utilized, (eg. the Compensator type utilized). It is also within the scope of the present invention Regression based Calibration Parameter evaluation Procedure to represent some Calibration Parameters with Global Parametric Functions, and to represent other Calibration Parameters discretely. Three examples of Global Parametric Function utilizing Models follow directly.

GLOBAL REGRESSION MODE (GRM) 1.

This (GRM) requires that five (5) Calibration Parameters be evaluated. Eqs. 45–47 provide equations for Predicted Fourier Data (PFD):

$$PFD_{p,n}(P, \Psi_n, \Delta_n, gP_s, gC_s, gA_s, g\delta(n, p_0, p_1)) \qquad (45)$$

$$\text{where } g\delta(n, p_0, p_1) = [p_0 \cdot 90 \cdot (1 + p_1/[w(n)]^2)]/w(n) \qquad (46)$$

$$\text{and } w(n) = C_0 + C_1 \cdot n + C_2 \cdot n^2 \qquad (47)$$

where w(n) returns a wavelength of electromagnetic radiation (in nanometers), corresponding to the "n"'th channel of a Photo Array, where C0, C1 and C2 are wavelength Calibration Parameters. In the case where a previously identified Ziess Diode Array Spectrometer Systems is utilized, said C0, C1 and C2 Calibration Parameters are provided by the manufacturer, and Eq. 47 can be utilized to provide Wavelength given a Photo Array Channel number.

The Global Retardance provided by a Compensator as a function of Wavelength is given by Eq. 46. Eq. 46 provides an Inverse Wavelength relationship, where "p0" is a Wavelength, (in nanometers), at which said Compensator is a "Quarter-Wave-Plate" and demonstrates a Ninety (90) degree Retardation, and "p1" accounts for the Dispersive effects in the Optical Properties of the Compensator. Higher order terms can be added to Eq. 46.

In this (GRM) Mode 1, the Azimuthal Offset Calibration Parameters are considered constant for all Wavelengths. Therefore, using (GRM) Mode 1, only Five (5) Global Calibration Parameters:

$$(gP_s, gC_s, gA_s, p_0, p_1),$$

in addition to Material System PSI and DELTA:

$$\Psi_n \text{ and } \Delta_n$$

need be evaluated by a present invention Regression Procedure.

GLOBAL REGRESSION MODE (GRM) 2.

This Mode is similar to (GRM) 1, but the $P_s$ Calibration Parameter is defined as a Global Calibration Parameter, (ie. it is a constant independent of Photo Array Channel Number "n"). Again, the Retardance of the Compensator is Parameterized by Eqs. 46 and 47. Values for Cs and As are allowed to take on discrete vales at each Photo Array Channel, however, Eq. 48 indicates the relationship:

$$PFD_{p,n}(P, \Psi_n, \Delta_n, gP_s, (C_s)_n, (A_s)_n, g\delta(n, p_0, p_1)) \qquad (48)$$

GLOBAL REGRESSION MODE (GRM) 3.

In this (GRM) 3 Mode, only Ps is defined as a Global Parameter, and all other system Calibration Parameters are allowed to take on discrete values at each Photo Array Channel. Eq. 49 indicates this relationship:

$$PFD_{p,n}(P, \Psi_n, \Delta_n, gP_s, (C_s)_n, (A_s)_n, \delta_n) \qquad 49$$

REGRESSION

The present invention Regression Analysis which evaluates the Calibration Parameters identified infra herein utilizes standard non-linear regression analysis. First a metric is defined by Eq. 50 to quantify Error between Calculated Predicted Fourier Data (PFD) and Experimentally Measured Fourier Data (MFD).

$$\chi^2 = \sum_P \sum_n \left( \frac{MFD_{P,n} - PFD(P, n, p_k)}{\sigma MFD_{P,n}} \right)^2 \qquad 50$$

Eq. 50 is a simplified way of stating that overall error between measured and predicted Calibration Data Sets is given by the squared difference between each measured and corresponding calculated predicted Fourier data, normalized by the approximate error at each measured data point ($\sigma MFD_{p,n}$), and summed over all the Polarizer and Wavelength (Channel) setting values. Eq. 51 provides a more riggerous mathematical definition.

$$\chi^2 = \sum_P \sum_n \left[ \left[ \frac{(m\alpha_2)_{P,n} - p\alpha_{2(P,n,p_k)}}{(\sigma\alpha_2)_{P,n}} \right]^2 + \left[ \frac{(m\beta_2)_{P,n} - p\beta_{2(P,n,p_k)}}{(\sigma\beta_2)_{P,n}} \right]^2 \cdots + \left[ \frac{(m\alpha_4)_{P,n} - p\alpha_{4(P,n,p_k)}}{(\sigma\alpha_4)_{P,n}} \right]^2 + \left[ \frac{(m\beta_4)_{P,n} - p\beta_{4(P,n,p_k)}}{(\sigma\beta_4)_{P,n}} \right]^2 \right] \qquad 51$$

In Eqs. 50 and 51, $p_k$ represents the "k" adjustable system Calibration Parameters required to calculate (PFD). The well known Marquardt-Levenberg non-linear Algorithm, as described in the Johs paper cited in the Background Section herein, can be used to itteratively adjust system Calibration Parameters $p_k$ to minimize error.

It is noted that good initial values are required to practice Regression which converges rapidly. The present invention obtains good starting values for use in the Global Regressions described, by performing a number of non-global Regressions at a multiplicity of discrete Wavelengths. The resulting ranges of values for the various Calibration Parameters then allows educated selection for Global Regression starting values.

It is also noted that Global Regression can be performed utilizing only data from every "N"'th Channel, (eg. every "N"'th Wavelength), to reduce required Regression procedure time to arrive at convergence. This approach to Regression is still to be considered as Global.

Once the present invention Spectroscopic Rotating Compensator Material System Investigation System is calibrated, it is possible to take data from unknown samples therewith and obtain PSI and DELTA plots therefore. Kleim et al., describes equations for PSI ($\Psi$) and DELTA ($\Delta$) and these equations are provided as Eq. 52 and 53 herein:

$$\tan(2\cdot\Psi) = \frac{\sqrt{[(\alpha_2)^2 + (\beta_2)^2]\cdot\left(\frac{1-\cos(\delta)}{\sin(\delta)}\right)^2 + 4\cdot(\beta_4\cdot\cos(2\cdot P) - \alpha_4\cdot\sin(2\cdot P))^2}}{2\cdot(\alpha_4\cdot\cos(2\cdot P) + \beta_4\cdot\sin(2\cdot P))} \quad 52$$

$$\tan(\Delta) = \left(\frac{1-\cos(\delta)}{2\cdot\sin(\delta)}\right)\cdot\frac{\alpha_2\cdot\sin(2\cdot P) - \beta_2\cdot\cos(2\cdot P)}{\alpha_4\cdot\sin(2\cdot P) - \beta_4\cdot\cos(2\cdot P)} \quad 53$$

In these equations the Analyzer should be set to +/−45 degrees. Also, prior to applying Eqs. 52 and 53 the measured Fourier Data should be transformed into "ideal" Fourier Data by application of Eqs. 15a, 15b, 16a, 16b, 17a and 17b as well as Eqs. 25–34. Kleim et al. also describes the advantages of performing a zone-averaged measurement in a Rotating Compensator System, (ie. averaging the PSI and DELTA extracted from measurements with the Analyzer A set to first, (+45) Degrees, and second to (−45) Degrees. This can be concurrently practiced with the present invention to further improve the accuracy of data measurement.

It is also noted that an alternative approach to obtaining Material System PSI and DELTA characterizing data, is to perform a Calibration Procedure on a present invention Spectroscopic Rotating Compensator Material System Investigation System in a Sample Present Mode, with said Material System present therein.

The present invention will be better understood by reference to the Detailed Description Section of this Disclosure, in conjunction with the accompanying Drawings.

SUMMARY OF THE INVENTION

It is therefore a purpose of the present invention to disclosed is a compensator/retarder system which allows adjustment to eliminate introduction of significant deviation and/or displacement into the propagation direction of a beam of electromagnetic radiation caused to interact therewith.

It is another purpose of the present invention to describe use of the present invention compensator/retarder in an ellipsometer/polarimeter systems in which it is caused to continuously rotate during use.

It is yet another purpose of the present invention to describe a method of calibration of an ellipsometer/ polarimeter system which includes a present invention compensator/retarder system.

BRIEF DESCRIPTION OF THE DRAWINGS

FIG. 1 diagramatically shows general ellipsometer system.

FIG. 2a demonstrates a "displacement" in a beam of electromagnetic radiation (LB') as compared to electromagnetic beam (LB) of radiation.

FIG. 2b demonstrates a "deviated" electromagnetic beam (LB') of radiation as compared to electromagnetic beam (LB) of radiation.

FIG. 3 shows, in upright side elevation, the present invention retarder system.

DETAILED DESCRIPTION

Figure 4:
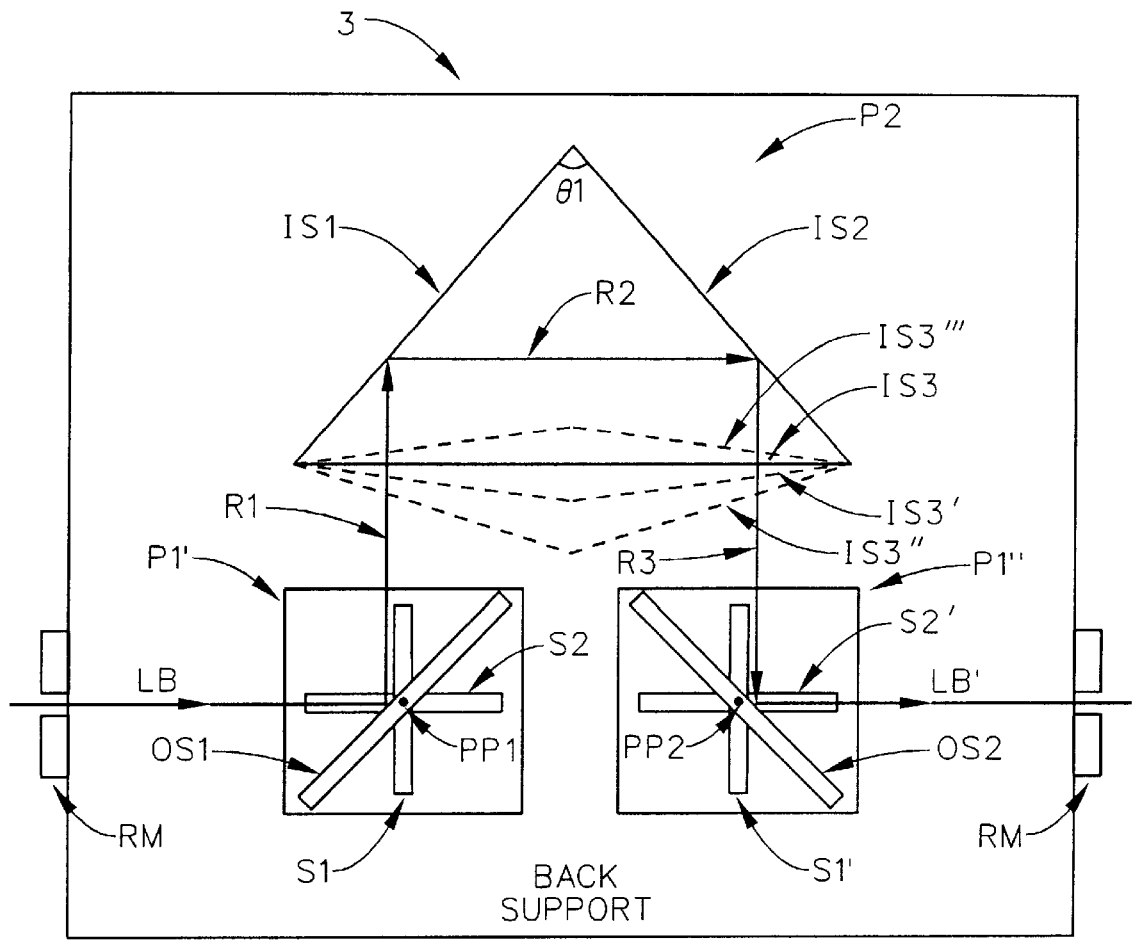
FIG. 4 shows an enlarged version of FIG. 3, with some additional attributes included.

Turning now to the Drawings, there is diagramatically shown in FIG. 1 a general ellipsometer system (1). Shown in functional sequence are:

a source of electromagnetic radiation (LS);
a polarizer (P);
at least one compensator (C1) (C2) (C3);
an analyzer (A); and
a detector system (DET);
where said polarizer, compensator and analyzer can each be variously, stationary, rotatable or rotating in use.

FIG. 1 shows that a beam of electromagnetic radiation (LBI), (after interaction with said Polarizer (P) and if present compensator (C1)), is caused to interact with a sample system (SS) and either reflect off thereof (LBO), or be transmitted therethrough (LBO') said sample system (SS) and enter a Detector (DET). Multiple compensators (C1) (C2) and (C3) are shown in dashed lines to indicate that only one, or more than one can be present. Electromagnetic radiation beam (EPCLB) is also shown exiting shown Analyzers (A) (A') and entering a Detector (DET).

The present invention provides a new compensator/retarder system which can be applied at (C1) and/or (C2) and/or (C3) as shown located in the FIG. 1 system.

Before presenting the present invention compensator/retarder system, to aide understanding as to why the present invention compensator/retarder system has utility, FIG. 2a is included to demonstrate a "displacement" in a beam of electromagnetic radiation (LB') as compared to electromagnetic beam (LB) of radiation. FIG. 2b is included to demonstrate a "deviated" electromagnetic beam (LB') of radiation as compared to electromagnetic beam (LB) of radiation. It should be appreciated then that the terms "displaced" and "deviated" indicate a change in the propagation direction of a beam of electromagnetic radiation. An important aspect of the present invention compensator/retarder system is that it is manufacturer, or user, adjustable to allow setting a condition wherein deviation or displacement between exit and incident beams of electromagnetic radiation do not exist, but rather said exit and incident beams of electromagnetic radiation are directly alligned with one another in a direction of propagation after interaction with the present invention compensator/retarder system. This is a very important result, particularly where a compensator/retarder system is caused to continuously rotate in use, as in rotating compensator ellipsometer or polarimeter systems.

Continuing, FIG. 3 shows that, in side elevation, the present invention compensator/retarder system (3) comprises a first element (P1), which as viewed in upright side elevation presents with first (OS1) and second (OS2) orientation adjustable mirrored elements which project at an angle with respect to one another. Said first element (P1) first (OS1) and second (OS2) orientation adjustable mirrored elements have reflective surfaces. Said compensator/retarder system (3) further comprises a nominally triangular shaped element (P2) which as viewed in side elevation presents with first (IS1) and second (IS2) sides which project to the left and right and downward from an upper point (UP2), said esssentially triangular shaped element (P2) is made of material which provides internally reflective, phase delay introducing, interfaces on first (IS1) and second (IS2) sides inside thereof. Said nominally triangular shaped element (P2) is oriented with respect to the first (OS1) and second (OS2) orientation adjustable mirrored elements such that in use an input electromagnetic beam of radiation (LB) caused to approach said first (OS1) orientation adjustable mirrored element along an essentially horizontally oriented propagation direction locus, is shown as being caused to reflect from, typically, an outer surface thereof and travel along as electromagnetic beam of radiation (R1) which is essentially upwardly vertically oriented. Next said electromagnetic beam of radiation (R1) is caused to enter said nominally triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by reflection from, typically, an outer surface of said second orientation adjustable mirrored element (OS2) of said first element (P1), such that said electromagnetic beam (LB') of radiation proceeds along an essentially horizontally oriented propagation direction locus, undeviated and undisplaced from the essentially horizontally oriented propagation direction locus of said input beam (LB) of essentially horizontally oriented electromagnetic radiation. This is the case even when said compensator/retarder system (3) is caused to rotate. The result of said described compensator/retarder system (3) application being that retardation is entered between orthogonal components of said input electromagnetic beam of radiation (LB), where it is caused to interact with the second (P2) element. Further, said second (P2) element is typically a right triangle, (with a ninty (90) degree angle at (UP2)), in side elevation as shown in FIG. 3, but it is noted that the bottom side IS3 can be other than a simple straight surface, (eg. see IS3'), and the outer surfaces of first (OS1) and second (OS2) orientation adjustable mirrored elements are typically, but not necessarily, made reflective by the presence of a coating of metal thereupon. A coating of metal serves assure a high reflectance and good electromagnetic beam radiation intensity throughput. Also, assuming accurately manufactured right angle (P2) nominally triangular shaped element is utilized, this compensator/retarder design provides inherent compensation of both angular and translational misalignments of the input light beam (LB), particularly where the first (OS1) and second (OS2) orientation adjustable mirrored elements are rotated as necessary about pivot points (PP1) and (PP2), respectively.

It is specifically noted that while the essentially totally internal reflections from said first (IS1) and second (IS2) sides of said esssentially triangular shaped element (P2) provides the retardation entered between orthogonal components of said electromagnetic beam (LB) of radiation, retardation can be entered by reflections from the first (OS1) and second (OS2) orientation adjustable mirrored elements.

As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the nominally triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the orientation adjustable mirrored elements of (P1) a polarimeter/ellipsometer in which said compensator/retarder (3) is present will require calibration to characterize the PSI-like component thereof.

FIG. 4 shows a larger version of FIG. 3, with some additional indications of acceptable variations on the shape of the the lower side of the nominally triangular shaped element (P2), (EG. (IS3) (IS3'), (IS3") & (IS3'")). Also indicated are adjustable modules (P1') & (P1") which are in place of (P1) in FIG. 3. The nominally triangular shaped element (P2) and the adjustable modules (P1') & (P1") are affixed to the (BACK SUPPORT) in generally acceptable locations. It is noted that FIG. 4 shows an angle Theta (θ1) at the top of the nominally triangular shaped element (P2), and it is noted that while said angle is typically ninty (90) degrees, it need not be so and it is to be understood that any functional angle is within the scope of the present invention. Adjustable Modules (P1') & (P1") have exemplary, (not limiting), provision to allow location of is orientation adjustable mirrored elements (OS1) & (OS2) pivot points, ((PP1) and (PP2) respectively, about which (OS1) and (OS2) can rotate in at least one plane), to be adjusted within slots ((S1) & (S2)) or ((S1') & (S2')), respectively. (It is noted that the pivots (PP1) and/or (PP2) can provide rotational motion capability in one or more planes) and functional equivalents which allow described and exemplified translational or rotational motion are to be considered within the scope of the present invention. The adjustment provided by basic placement of (P1') and (P1") and (P2) on said (BACK SUPPORT), in combination with available translational and rotational adjustment of (OS1) & (OS2) within (P1') and (P1"), respectively, allows a user to very accurately allign the present invention compensator/retarder system (3) such that that electromagnetic beam (LB') of radiation exits the present invention compensator/retarder (3) in the essentially same propagation direction as does electromagnetic beam (LB) of radiation enter thereinto. FIG. 4 also shows Rotation Means (RM) at right and left sides thereof which are shown to represent that the present invention compensator/retarder system (3) has the functional capability of being rotated about the propagation direction of said undeviated and undisplaced exit and incident beams of electromagnetic radiation (LB) & (LB').

It is noted that while FIGS. 3 and 4 show electromagnetic beams (LB) & (LB') of radiation as externally reflecting from an "external" surface of adjustable mirrored elements (OS1) & (OS2), such is to be broadly interpreted to include a functionally equivalent system in which the mirrored surface is "internal", thereby requiring at least one of said electromagnetic beams (LB) & (LB') of radiation to transverse the depth of an adjustable mirrored elements (OS1) & (OS2), reflect from the "internal" "back" surface thereof, and transverse the depth of an adjustable mirrored elements (OS1) & (OS2) as it propagates.

To provide additional insight to a utility providing application of a present invention compensator/retarder system, the following material which is found in co-pending patent application Ser. No. 08/912,211 is included to better describe rotating compensator ellipsometer systems.

Figure 5:
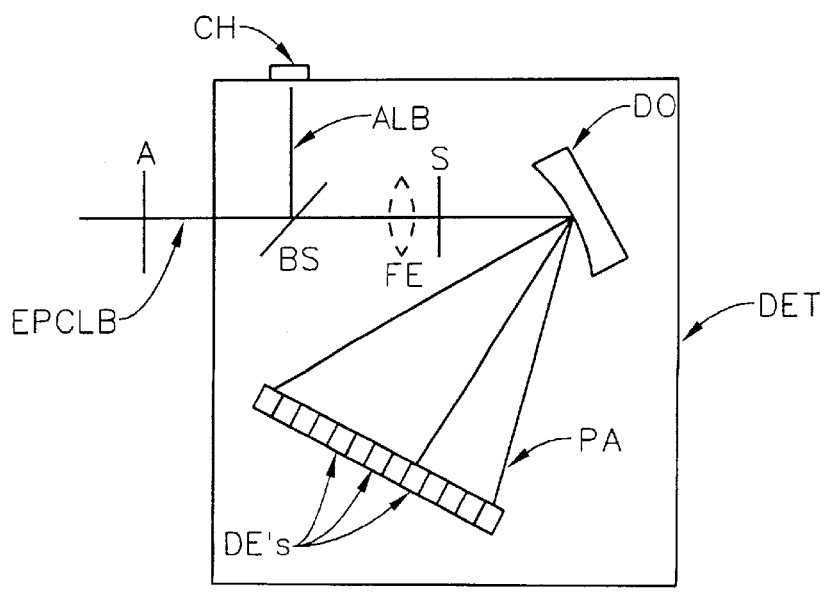
FIG. 5 shows an exemplary beam splitter and cross hair containing reticule alignment means which is useful in electromagnetic beam alignment in present invention ellipsometer and polarimeter systems.

Continuing, a utility providing rotating compensator ellipsometer system as indicated in FIG. 1 utilizes a Polychromatic Source of Electromagnetic Radiation (LS), and FIG. 5 shows that the Detector System can comprise Element (DE's) containing Photo Array. In use a Dispersive Optics (DO) receives a Polychromatic Electromagnetic Beam (EPCLB) which has interacted with a Material System (MS) and passed through said Analyzer (A), and diffracts said Polychromatic Electromagnetic Beam (EPCLB), such that each Photo Array (PA) Diode Element (DE) intercepts an Essentially Single Wavelength, (eg. a small band of wavelengths centered about a central single wavelength). Note that a Focusing Element (FE) is shown in a dashed line format to indicate that its presence is optional. The Focusing Element (FE), when present, serves to provide a focused Polychromatic Beam of Electromagnetic Waves at the input to said Detector Elements (DE's) containing Photo Array etector System (DET), and the Detector System (DET) provides signals developed by the Diode Elements (DE's) in a sequential output or a parallel output from the Diode Elements (DE's). It is emphasized that a preferred Detector Elements (DE's) containing Photo Array Detector System (DET) is an "Off-the-Shelf-System" which includes a Focusing Element (FE), and provides a self contained Dispersive Optics (DO) and Diode Element (DE) Array. The "Off-The-Shelf-System" of said preferred embodiment of the present Rotating Compensator Material System Investigation System is a Zeiss Diode Array Spectrometer System identified by manufacturer numbers in the group: (MMS1 (300–1150 nm); UV/VIS MMS (190–230 nm); UV MMS (190–400 nm); AND IR MMS (900–2400 nm)). Said identified Zeiss systems provide a very compact system comprising a multiplicity of Detector Elements (DE's), and provide focusing via a Focusing Element (FE), Slit (S), and single concave holographic grating dispersive optics (DO), as generally represented by FIG. 5.

Note that FIG. 5 also shows the presence of a Beam Splitter (BS) and a Cross Hair containing Reticule (CH) in the Detector Elements (DE's) containing Photo Array Detector System (DET). If the Beam Splitter (BS), the Dispersive Optics (DO), the Focusing Element (FE), the Detector Elements (DE's) containing Photo Array (PA), and the Cross Hair containing Reticule (CH) are mounted so as to move as a rigid unit, then it should be appreciated that causing an Alignment Electromagnetic Radiation Beam (ALB) which reflects to said Cross Hair containing Reticule (CH) to be present near a Cross Hair crossing point can effect good alignment of the Detector Elements (DE's) containing Photo Array Detector System (DET) with respect to an entering Polarized Beam of Electromagnetic Radiation (EPCLB). In practice such an arrangement has been found to work very well. It is further noted that the element identified as (CH) could represent a Quadrature Photodetector and Automatic Alignment Means, or other functionally suitable system.

It is also noted that, as regards basic operation of the a present invention rotating compensator ellispsometer system, a present invention Compensator (C) (C'), (C") as shown in FIGS. 3 and 4 can be functionally replaced by an Off-the-Shelf Quarter-Wave-Plate with its Optical Axis in the plane of a surface thereof, (see FIG. 12e), or Berek-type with its Optical Axis perpendicular to a surface thereof, (see FIG. 12d), and is selected without special concern to its Achromatic Operating Characteristics, emphasis added. Note that a Zero-Order Waveplate can be constructed from two (2) Multiple-Order Waveplates of different thicknesses (T1) and (T2) which have Optical Axes oreinted Ninety (90) degrees to one another, such that the overall effect of retardation in in the Zero-Order, (see FIG. 12f). As well, said Compensator (C), (C'), (C") can be made of essentially any functional material such as Quartz or Polymer etc.

The present invention compensator/retarder system as shown in FIGS. 3 and 4 is preferred because in addition to the Present Invention Rotating Compensator Material System Investigation System being Spectroscopic, (ie. simultaneously operates on a number of Wavelengths in a Beam containing many Electromagnetic Wavelengths, over a range of, for instance, 190–1000 nanometers, and a Compensator (C), (C'), (C") utilized therein can provide a Retardance which, for instance, varies inversely with Wavelength and still be usable), a present invention Compensator (C), (C'), (C") must allow passage of a Polychromatic Electromagnetic Beam therethrough without causing significant Attenuation, Deviation or Displacement in the Direction of Propagation thereof. If this is not the case, difficult to compensate complexities are caused in Detector Elements (DE's) containing Photo Array Detector System (DET) Detector Element Output Signals.

Figure 10:
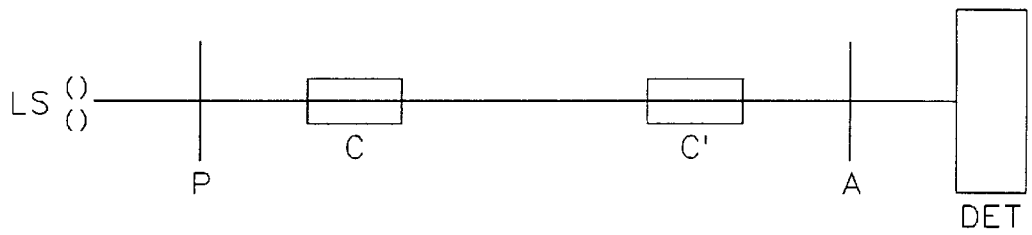
FIG. 10 demonstrates a rotating compensator material system investigation system shown in a "straight-through" configuration.

Continuing, the reason the Present Invention can operate with a Compensator (C), (C'), (C") that does not provide even close to a Constant Ninety (90) Degree Retardance over a range of Wavelengths, (which would constitute Ideal Characteristics), is that a Regression based Calibration Procedure utilized, (see the Disclosure of the Invention Section of this Specification), provides Wavelength dependent Compensation effecting values for Calibration Parameters as required in a developed Mathematical Model of the present invention Rotating Compensator Material System Investigation System. As better described in the Disclosure of the Invention Section of this Disclosure, the Inventors develop a Calibration Parameter Containing Mathematical Model of the present invention Rotating Compensator Material System Investigation System by, for instance, utilizing Matrix Representations for various System Components involved, then multiplies out the Matrices in an appropriate order to provide a Transfer Function. This applies for all Wavelengths monitored by a Detector Elements (DE's) containing Photo Array Detector System (DET) Detector Element (DE). Next, Data Set(s) are Experimentally obtained as a function of wavelength and typically as a function of various settings of the Polarizer (P) or Analyzer (A), (or both could be rotated to various positions), while a Compensator (C) rotates at, typically though not necessarily, Twenty (20) to Thirty (30) Hz. Other rotation speeds can be utilized and if two Compensators are present one or both can be caused to rotate, and if both are caused to rotate, as mentioned infra herein, they can be caused to rotate at the same, or different, speeds. (Note that Data Set(s) could also be achieved utilizing variation of Angle-Of-Incidence of a Beam of Polychromatic Radiation with respect to a Material System under investigation). Calibration Parameters in the Mathematical Model are then evaluated by, typically, Mean-Square-Error based Regression onto the Data Set(s). It is also possible to effectively find Calibration Parameter containing Mathematical Expressions for Coefficients of Mathematical Series, (eg. Fourier Series), which comprise the Mathematical Model Transfer Function, and calculate Numerical Values for the Coefficients from the Data Set(s), then effectively perform Regression of said Calibration Parameter containing Mathematical Expressions for Coefficients of Mathematical Series Transfer Function onto said Numerical Values for the Coefficients from the Data Set(s). It is emphsized that a single Two-Dimensional Data Set has been found sufficient to allow excellent Calibration results to be achieved. Said Two-Dimensional Data Set typically is Intensity vs. Wavelength, and Polarizer or Analyzer Azimuthal Rotation Angle settings. In addition, said Two-Dimensional Data Set can be obtained from a present invention Rotating Compensator Material System Investigation System oriented so that a Polychromatic Beam of Electromagnetic Radiation interacts with a Material System (ie. the "Sample Present" Mode - - - see FIGS. 1, 6, 7, and 8)), or such that said Polychromatic Beam of Electromagnetic Radiation passes through the present invention Rotating Compensator Material System Investigation System without interacting with a Material System, other than a Material System comprised of "Open Atmosphere", (ie. the "Straight-Through" Mode - - - see FIG. 10). The present invention Rotating Compensator Material System Investigation System can also, of course, be Calibrated utilizing more than one Data Set as well, but as alluded to, this has not been found necessary. This is mentioned as the invention reported in Co-pending patent application Ser. No. 08/618, 820, wherein a Rotating Compensator Material System Investigation System utilized in the Infra-red band of wavelengths, requires that two (2) Data Sets be present, (eg. selected with the Rotating Compensator Material System Investigation System oriented in a manner selected from the group: ("Straight-Through", "Material Sample Present", "Alternative Material Sample Present")). Both Data Sets are simultaneously utilized in a Regression Procedure to evaluate numerous Calibration Coefficients in a Mathematical Model which is described in the application Ser. No. 08/618, 820. The reason that only one (1) Data Set is typically required to practice the described present invention Calibration Procedure, is that the number of Calibration Parameters required by the Mathematical Model of the present invention, (which is usually not operated in the Infra-red range of wavelengths), is much fewer that the number of Calibration Parameters required by the Mathematical Model of the Rotating Compensator Material System Investigation System operated in the Infra-red range of wavelengths. The present invention Rotating Compensator Material System Investigation System Mathematical Model typically involves as few as Five (5) Calibration Parameters, (where only one Compensator is present), in combination with simultaneous determination of a Material System PSI and DELTA. (It is noted that a straight-through mode essentially provides open atmosphere as a Material System and that the PSI and DELTA of open atmosphere are forty-five (45) degrees and zero (0.0) degrees, respectively). Said Five (5) Calibration Parameters are Azimuthal Orientation Angles for Polarizer (Ps), Analyzer (As), Compensator (Cs), and Compensator Retardance Parameters (P0) and (P1). Equations (45) and (46) serve as further demonstratration of this point. (Note that the (Ps), (Cs) and (As) Azimuthal Orientation Calibration Angles can be thought of as serving to align the Polarizer, Compensator and Analyzer Azimuths with a Material System Frame of Reference). Of course, if two Compensators are present then an additional Compensator Orientation Angle (Cs2) and Compensator Retardance Parameters (P0') and (P1') and additional would also have to be evaluated. (It is noted that Retardation entered between orthogonal components of a Polarized Electromagnetic Beam, by a Compensator, is accounted for by a Matrix Component, and typically the r4 term of a Jones Matrix, (see Disclosure of the Invention Section of this Disclosure), but such is accounted for by Compensator Retardation Parameters (P0), (P1), (P0'), (P1') in the presently described Calibration Procedure).

Figure 6:
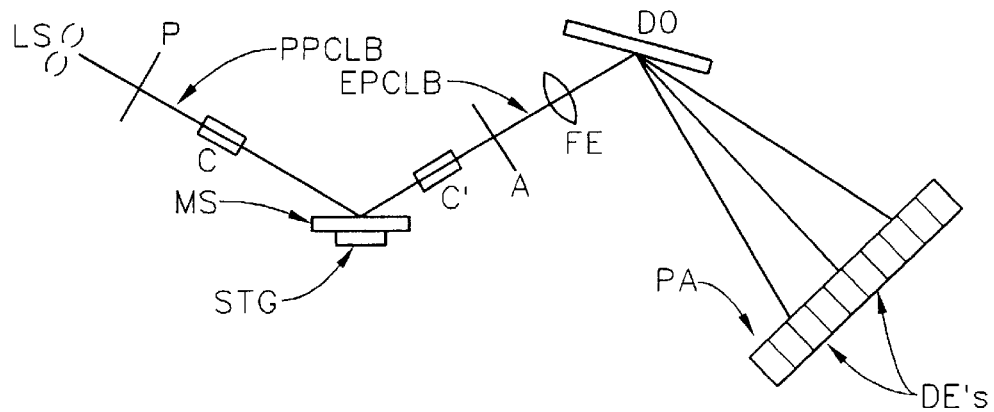
FIG. 6 shows a spectroscopic reflectance mode version of the rotating compensator material system investigation system shown in FIG. 1, with the FIG. 5 detector elements (DE's) containing photo array detector system (DET) shown present directly after the analyzer (A).

Now, it is to be understood that the system of the present invention Spectroscopic Rotating Compensator Material System Investigation System is basically found in a combination of components shown in FIGS. 1 and 5, the basic result of said combination, for a Reflectance Mode System, being shown in FIG. 6. That is, FIG. 6 shows a Spectroscopic Reflectance Mode version of the Rotating Compensator Material System Investigation System shown in FIG. 1, with the FIG. 5 Detector Elements (DE's) containing Photo Array Detector System (DET) shown present directly after the Analyzer (A).

Figure 7:
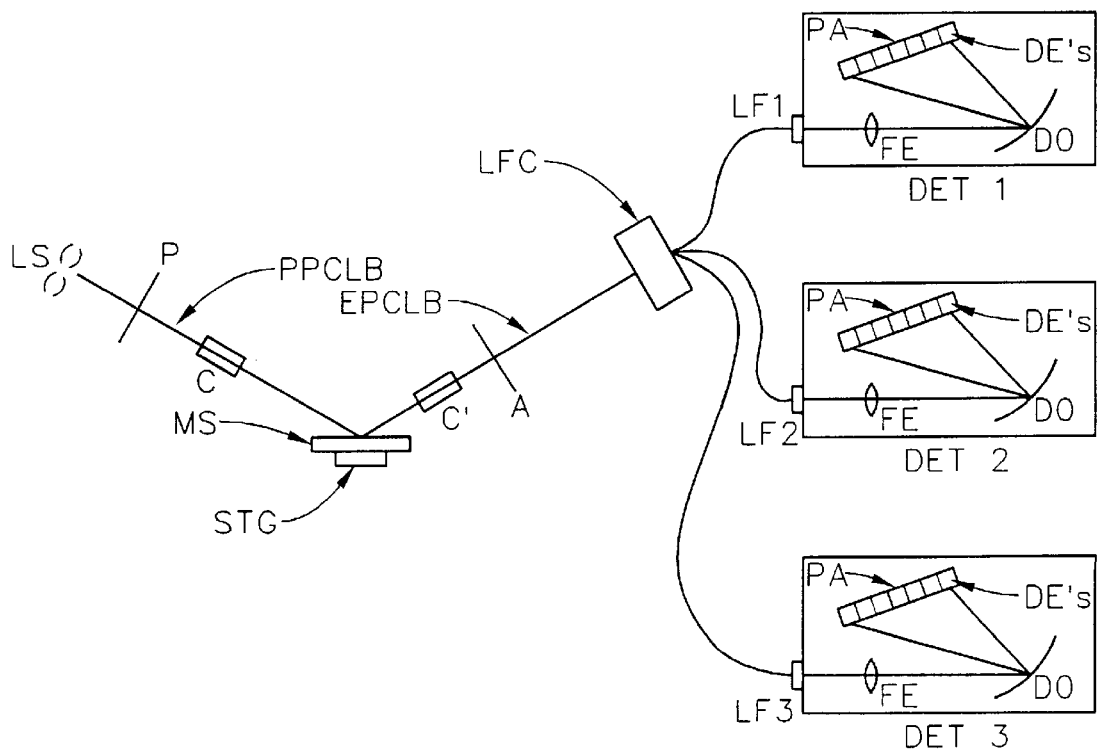
FIG. 7 shows another present invention system reflectance mode system configuration in which three (3) detectors (Det 1), (Det 2) and (Det 3) are fed input by fiber optics (LF1), (LF2) and (LF3) as shown in FIG. 12c.

FIG. 7 shows another present invention system Reflectance Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A). (Note that a FIG. 12c at least Bifrucated Fiber Optic could be utilized). Said three (3) Detectors (Det 1), (Det 2) and (Det 3) can be previously disclosed Off-the-shelf Zeiss Diode Array Spectrometers, and can each comprise a Focusing Element (FE) in functional combination with a Dispersive Optics (DO) and a Diode Element (DE) containing Photo Array (PA).

Figure 8:
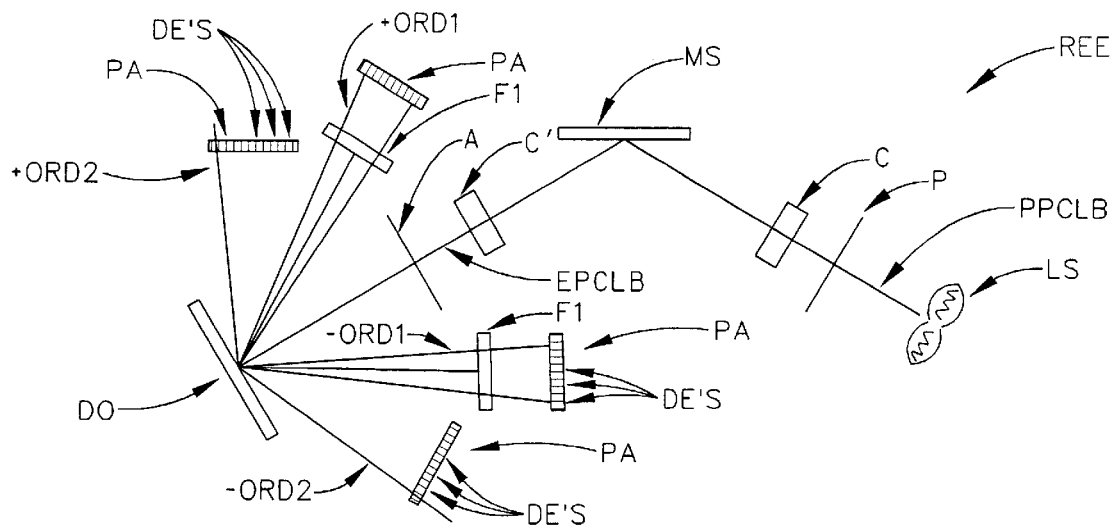
FIG. 8 shows that the present invention can cause a polychromatic beam of polarized electromagnetic radiation (PPCLB) to, after interaction with a material system (MS), reflect therefrom and impinge upon a dispersive optics (DO), (eg. a diffraction grating), such that a plurality of Orders (+ORD2, +ORD1, −ORD1 and −ORD2) are produced.

FIG. 8 shows that the present invention can cause a Polychromatic Beam of Polarized Electromagnetic Radiation (PPCLB) to, after interaction with a Material System (MS), reflect therefrom. FIG. 8 shows that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, −ORD1 and −ORD2) are produced. Each said Order is comprised of a spectrum of Wavelengths, and FIG. 8 shows that Wavelengths in said Orders (+ORD2, +ORD1, −ORD1 and −ORD2) can be intercepted by Detector elements (DE's) in Photo Arrays (PA). The present invention can, in some embodiments, utilize such a system. It is noted that the Dispersive Optics (DO) is typically rotatable so that the direction each Order of wavelengths generally proceeds from said Dispersive Optics (DO) is adjustable. Note that FIG. 8 also shows the presence of Filters (F1). It is noted that Wavelengths for adjacent Orders overlap, and said Filters (F1) allow a user to pass only desired Wavelengths, as well as reduce background radiation entry to Photo Arrays (PA's). Typically a Focusing Element is not present in a FIG. 8 embodiment.

It is also noted that Fiber Optics can be utilized to carry Polychromatic Electromagnetic Radiation from a Source thereof (LS) to the position of a Polarizer (P), or from the position of an Analyzer (A) to a Detector (DET) in FIGS. 1, 6, 7 and 8.

Analogically similar figures to those shown in FIGS. 6–8, but oriented for use in a Transmission Mode are not shown, but should be understood as within the scope of the present invention as implied by FIG. 1.

Figure 11A:
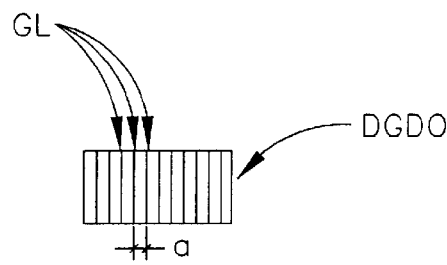
FIG. 11a shows a lined geometry diffraction grating.
Figure 11B:
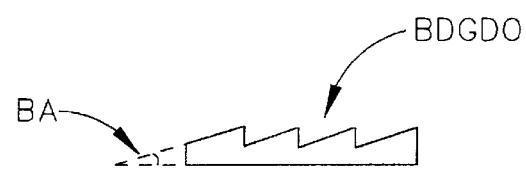
FIG. 11b shows a "blazed" geometry Diffraction Grating Dispersive Optics.
Figure 11C:
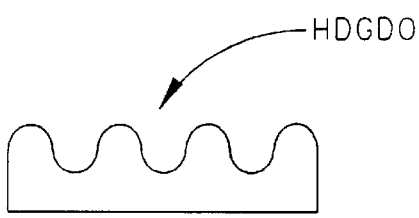
FIG. 11c shows a cross-sectional view of a holographic diffraction grating dispersion optics.
Figure 11D:
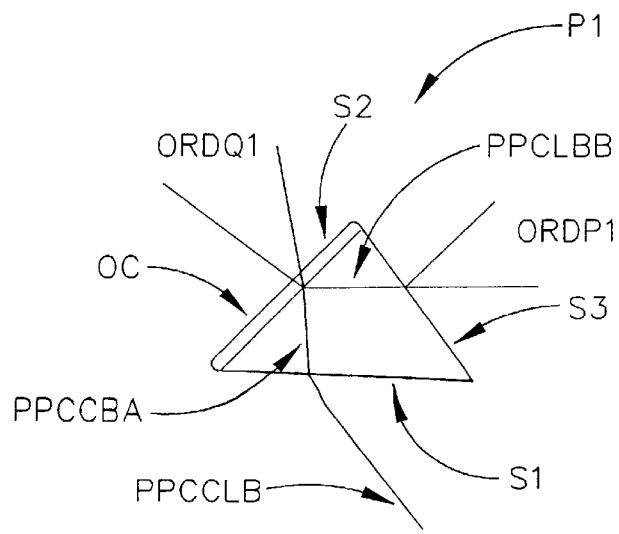
FIG. 11d shows a prism dispersive optics.

For general information, FIGS. 11a through 11d show various Dispersive Optics geometries. FIG. 11a shows a lined geometry diffraction grating (DGDO). The grating lines (GL) are essentially rectangular in cross-section with a spacing (a) therebetween. FIG. 11b shows a "Blazed" geometry Diffraction Grating Dispersive Optics (BDGDO). The Blazing Angle (BA) shifts reflected diffracted energy between "Orders" such into +ORD1 and −ORD1 from a typically useless ORDO which projects perpendicularly back from the surface of said Dispersive Optics shown in FIG. 8. FIG. 11c shows a cross-sectional view of a Holographic Diffraction Grating Dispersion Optics (HDGDO) as is present in the Off-the-Shelf Zeiss Diode Array Spectrometer systems identified infra herein. (Said Zeiss Systems utilize a Holographic configuration in a concave shaped system). FIG. 11d shows a Prism Dispersive Optics (P1), with a Polarized Polychromatic Electromagnetic Beam (PPCCLE) entering Side (S1), and exiting Side (S2) and Side (S3) as Diffracted Beams in two "Orders" (ORDQ1) and (ORDP1) respectively. Note that a coating (OC) causes partial internal reflection of beam (PPCCBA) into beam (PPCLBB) to produce two "Orders". Any functional Diffraction effecting element can be utilized as a Dispersive Optics (DO) in the present invention.

Figure 12A:
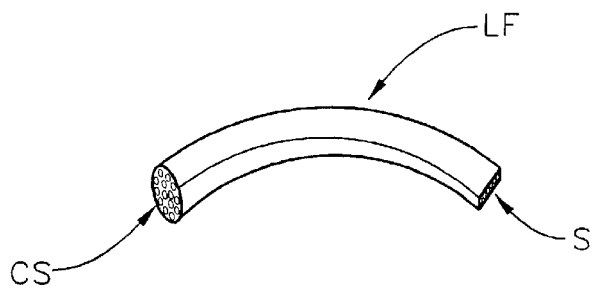
FIG. 12a shows a fiber optic which is essentially circular at the left side and which becomes of a "slit" shape at the right side.
Figure 12B:
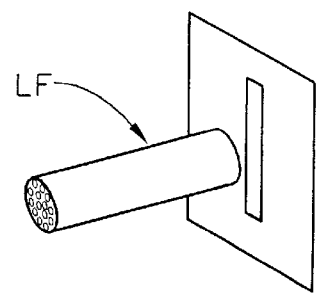
FIG. 12b shows a fiber optic which is essentially circular shaped along the entire length thereof, and which provides input to a "Slit" per se.
Figure 12C:
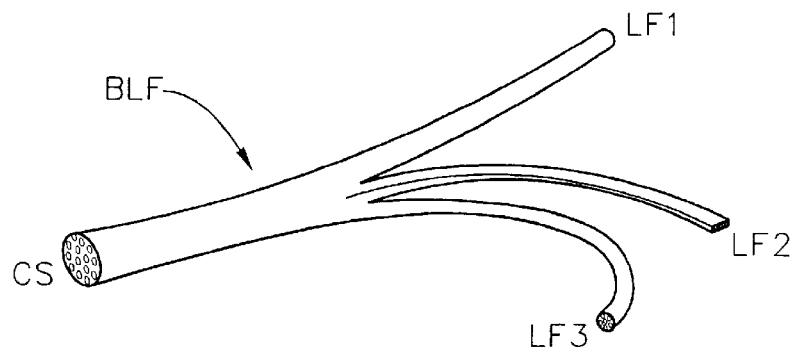
FIG. 12c shows a trifrucated fiber optic which is essentially circular at the left side, which trifrucates and then is exemplified as becoming circular or a of a "slit" shape at the right side.
Figure 12D:
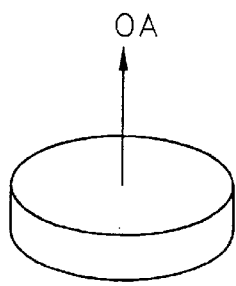
FIG. 12d shows a berek-type retarder with its optical axis perpendicular to a surface thereof
Figure 12E:
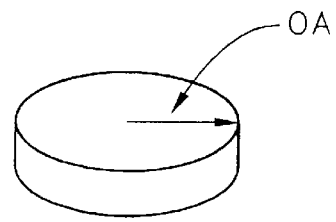
FIG. 12e shows a quarter-wave-plate retarder with its optical axis in the plane of a surface thereof.
Figure 12F:
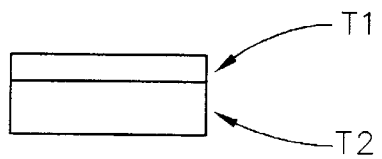
FIG. 12f shows a zero-order waveplate constructed from two (2) multiple-order waveplates of different thicknesses (T1) and (T2) which have optical axes oreinted ninty (90) degrees to one another

As the present invention can utilize Fiber Optics, certain geometries thereof are shown in FIGS. 12a through 12c. FIG. 12a shows a Fiber Optic which is essentially circular at the left side and which becomes of a "slit" shape at the right side. FIG. 12b shows a Fiber Optic which is essentially circular shaped along the entire length thereof, and which provides input to a "Slit" per se. The effects achieved by the Fiber Optics in FIGS. 12a and 12b are similar. FIG. 12c shows a Trifrucated Fiber Optic which is essentially circular at the left side, which trifrucates and then is exemplified as becoming circular or a of a "slit" shape at the right side. Use of an effectively Trifrucated Fiber Optics is shown applied in FIG. 7. (Noted that present invention Optical Fibers are utilized only as convenient means by which to transport electromagnetic radiation and not to modify polarization state).

PRESENT INVENTION METHOD OF CALIBRATION (Note, the Calibration Method of the present invention is better described in the Disclosure of the Invention Section of this Specification. The following is to be considered as supplemental to the description provided in said Disclosure of the Invention Section).

In use, the present invention Spectroscopic Rotating Compensator Material System Investigation System is modeled mathematically, with Calibration Parameters being included in said Mathematical Model. Said Calibration Parameters are evaluated by a regression based approach based upon Data Set(s) obtained at a multiplicity of Angles-of-Incidence, and/or Wavelengths and/or Polarizer or Analyzer Rotation Angle Settings etc. (Note that a relatively easily obtained Two Dimensional Data Set as a function of Wavelength, and either Polarizer or Analyzer Azimuthal Angle Setting, is greatly preferred and has been found to be sufficient). As mentioned infra herein, typically, Matrix representations of the Polarizer (P), Compensator (C), Analyzer (A), are utilized, with calibration parameters appearing in Matrix Components. Once evaluation of the Spectroscopic Rotating Compensator Ellipsometer System (RC) Calibration Parameters is effected, a Material System (MS) can be subjected to investigation thereby, with otherwise unexplained changes effected in a Beam of Polarized Electromagnetic Radiation (LB), present after interaction with a Material System (MS), being attributed to said Material System (MS). (It is also to be noted that PSI and DELTA associated with a Material System at a specific Angle-Of-Incidence can be simultaneously evaluated with Calibration Parameter values if a Data Set is obtained utilizing a Material System present mode and the Mathematical Model includes said Material System PSI and DELTA as Fit Parameters).

Figure 9:
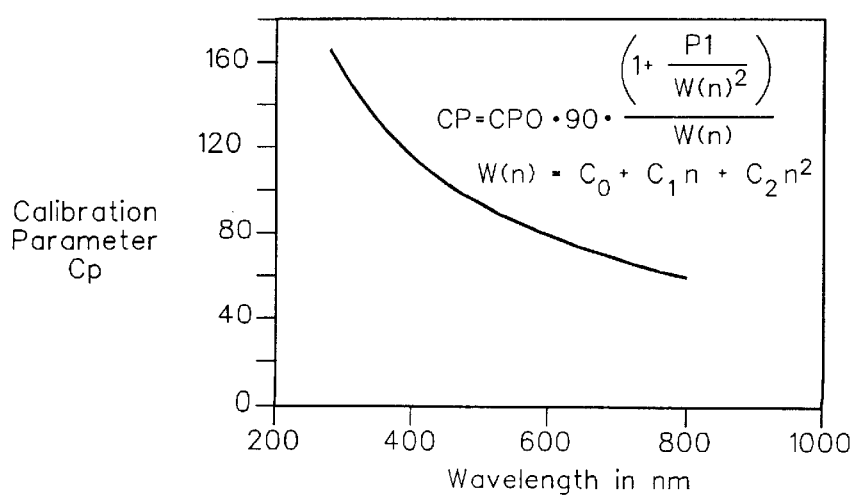
FIG. 9 demonstrates a present invention "Parameterization" approach to modeling Calibration Parameters in a Mathematical Model.

FIG. 9 demonstrates a present invention "Parameterization" approach to modeling Calibration Parameters in a Mathematical Model. It must be understood that Calibration Parameters are often a function of Wavelength. For instance, the Retardation provided by a Compensator often varies inversely with wavelength. Where this is the case typical Mathematical Regression based evaluation of Calibration Parameters requires that a value for a Calibration Parameter be determined at each wavelength monitored. However, FIG. 9 shows that a plot of a Calibration Parameter vs. Wavelength can yield a locus which can be accurately modeled by a Mathematical Equation which requires only a few constants be known to allow calculation of the Calibration Parameter at a given Wavelength. For instance, FIG. 9 shows that a value for a Wavelength W(n) can be calculated knowing a Channel Number (n), (ie. Diode Element in an Array, such as shown in FIGS. 5–8), from which a signal is obtained, and values for three constants C0, C1 and C2. Knowing values for Parameters CP0 and P1 as well allows calculating a Calibration Parameter Value (CP) given a Diode Element Array Channel Number number (n). It can occur that (n) is two-hundred (200) or more and if a non-Parameterized approach to calibration is utilized, two-hundred (200) or more values for Calibration Parameter CP would have to be determined and stored. However, utilizing the Calibration Parameter Parameterization approach, it can be seen that a Regression procedure must return values for only Two (2) variables, (CP0 and P1). Also, if a Calibration Procedure were selected to include Angle-Of-Incidence (AOI) as a Data Set variable, it is known that where a Calibration Procedure utilizes a "Material System Present" configuration for acquiring data, that the PSI and DELTA values for the Material System will vary with said (AOI). (Note, said PSI and DELTA are equivalent to Calibration Parameters in a Regression procedure which serves to evaluate Calibration Parameters based upon Data obtained with a Material System present approach). A similar Parameterization approach could be applied to provide equations for calculating a PSI and a DELTA value given an (AOI), each of said equations involving only a few variables which would have to be evaluated by a Regression procedure. (Note, the concept of "Parameterization" is often encountered in the modeling of Dielectric Functions, wherein one or more Lorentz Oscillator(s) is/are utilized. Lorentz Oscillator Structures require only a Magnitude and a Broadening Calibration Parameter be evaluated to be fully defined. Some peak regions of a Dielectric Function can be adequately modeled by said two evaluated Calibration Parameters, however, the peak and tail regions of a Lorentz Oscillator Structure are not mathematically separate and while a Lorentz Oscillator Structure might adequately define a peak region in a Dielectric Function plot, it is often inadequate in non-peak regions. This problem is the focus in Co-pending patent application Ser. No. 08/514,959 which teaches Finite Width Oscillator Structures comprised of Finite Order Polynomials and/or Finite Magnitude Essentially Zero Width Discontinuities as replacement for Lorentz Oscillator Structures). The present invention, where beneficial, utilizes Parameterization of Calibration Parameters. That is, where a plot of a Calibration Parameter vs. a Data Set Independent Variable demonstrates that Parameterization can be applied with benefit, the present invention Parameterization of Calibration Parameter approach, with respect to some Data Set Independent Variable, can be applied.

The present invention is then comprises a preferred compensator/retarder system as shown in FIGS. 3 and 4; a Spectroscopic Rotating Compensator Material System Investigation System comprised of Components as identified in FIGS. 1–8, and the present invention includes a Calibration Method which utilizes Regression, including Parameterization of Calibration Parameter where desired and beneficial, to evaluate Calibration Parameters in a Mathematical Model of said Spectroscopic Rotating Compensator Material System Investigation System.

It is also to be appreciated that utility is provided by a Spectroscopic Rotating Compensator Material System Investigation SYSTEM known which comprises at once:

1. at least one present invention non-Achromatic Characteristic Rotating Compensator (RC);
2. a Dispersive Optics (DO); and
3. a Detector Elements (DE's) containing Detector System (DET) which comprises a Photo Array (PA); such that in use a Multiplicity of Material System (MS) Investigation Wavelengths in a Polychromatic Beam of Electromagnetic Wavelengths are simultaneously Monitored.

Spectroscopic Rotating Compensator Material System Investigation System utilizes a, (possibly Calibration Parameter Parameterization aided), Mathematical Regression based METHOD approach to Evaluation of Calibration Parameters in a Mathematical Model of such a Spectroscopic Rotating Compensator Material System Investigation System, such that application thereof allows compensating the Non-Achromatic, and other non-Ideal, aspects of a present Rotating Compensator.

The present invention conveniently provides, in a commercially realizable format, that which was thought to be, prior to the present invention, essentially impossibly to provide in other than a prohibitively expensive, (and perhaps difficult to calibrate and utilize), single unit format.

It is to be understood that a Photo Array can be comprised of Diode-Elements, Charge-Coupled-Devicies, Bucket-Brigade-Devices and equivalents.

It is also noted that Polychromatic Electromagnetic Beam Source can be comprised of a combined plurality/multiplicity of Laser Sources, and that Polychromatic Electromagnetic Beam Source can include an effective Polarizer therewithin, thereby eliminating the need for a separate Polarizer. Such cases are to be considered within the scope of the Claims. It is also to be understood that the terminology "Achromatic" is to be understood to mean that an uncertianty in Retardance provided by a Compensator of One (1.0) Degree will effect an uncertianty of One-Quarter (¼) Degree in a measured Sample System (PSI), and an uncertianty of One-Half (½) Degree in a measured Sample System (DELTA), (as provided by Eq. 58 in the previously cited Kleim reference).

As alluded to infra herein, the present invention compensator/retarder system finds particulary relevant, but not limiting, application in rotating compensator ellipsometer and polarimeter systems, which, it is noted, do not demonstrate "blind-spots" at DELTA'S of zero (0.0) and one-hundred-eighty (180) degrees, (as characteristic of rotating polarizer or analyzer systems), or PSI of forty-five (45) degrees, (as characteristic of modulation element systems).

Having hereby disclosed the subject matter of the present invention, it should be apparent that many modifications, substitutions, and variations of the present invention are possible in light thereof. It is to be understood that the present invention can be practiced other than as specifically described and should be limited in scope and breadth only by the appended Claims.

We claim:

1. A compensator/retarder system comprising:
as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation.

2. A compensator/retarder system as in claim 1, which comprises means for imparting at least one of:

translational; and rotational;

motion, in at least one dimenstion, to at least one of said first and second orientation adjustable mirrored elements.

3. A spectroscopic ellipsometer/polarimeter system comprising a compensator/retarder which comprises:

as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation.

4. A spectroscopic ellipsometer/polarimeter system comprising in sequence:

a source of electromagnetic radiation;

a polarizer system;

a compensator/retarder;

an analyzer; and a detector system;

said compensator/retarder comprising, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

such that in use a beam of electromagnetic radiation is provided by said source of electromagnetic radiation and is caused to pass through said polarizer system, then interact with, in a functional sequence selectee from the group consisting of:

a sample system and said compensator/retarder system; and, said compensator system and a sample system;

and pass through said analyzer and enter said detector system.

5. A method of practicing ellipsometry/polarimetry comprising the steps of:

a. providing a spectroscopic ellipsometer/polarimeter system sequentially comprising:

a source of electromagnetic radiation;

a polarizer;

a compensator/retarder system comprising, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

an analyzer system; and a detector system;

b. placing a sample system into said spectroscopic ellipsometer/polarimeter system;

c. causing said source of electromagnetic radiation to provide a beam of electromagnetic radiation to said sample system; and d. detecting said beam of electromagentic radiation after interaction thereof with said sample system.

6. A method of practicing ellipsometry/polarimetry as in claim 5 which further comprises the step of causing said compensator/retarder system to rotate during use about the propagation direction locus of said input beam of essentially horizontally oriented electromagnetic radiation.

7. A method of practicing ellipsometry/polarimetry as in claim 5 which further comprises the step of adjusting the orientation of said first and second orientation adjustable mirrored elements so that an electromagentic beam which is caused to exit from said compensator/retarder system is undeviated and undisplaced from the locus of said input beam of electromagnetic radiation, even when said compensator/retarder system is caused to rotate.

8. A method of practicing ellipsometry/polarimetry as in claim 5 which further includes the step of changing the orientation of said spectroscopic ellipsometer/polarimeter system so that a beam of electromagentic radiation entered thereto is not oriented horizontally with respect to an external frame of reference, but so that relative relationships between said first and second orientation adjustable mirrored elements and said third element are maintained.

9. A method of practicing ellipsometry/polarimetry as in claim 8 which further comprises the step of causing said compensator/retarder system to rotate during use about the propagation direction locus of said input beam of electromagnetic radiation which is no longer oriented horizontally with respect to said external frame of reference.

10. A compensator/retarder system comprising:

first and second orientation adjustable mirrored elements which each have reflective surfaces; said compensator/retarder system further comprising a third element which presents with first and second sides which project at an angle with respect to one another from a common point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements, is caused to externally reflect therefrom and enter said third element and essentially totally internally reflect from one of said first and second sides thereof, then essentially totally internally reflect from the other of said first and second sides and then proceed to and reflect from the other of said first and second orientation adjustable mirrored elements and proceed along a propagation direction locus which is essentially undeviated and undisplaced from that of said input electromagentic beam of radiation, even when said compensator/retarder is caused to rotate; with a result being that retardation is entered between orthogonal components of said input electromagnetic beam of radiation.

11. A compensator/retarder system as in claim 10 which comprises means for imparting at least one of:

translational; and rotational;

motion, in at least one dimenstion, to at least one of said first and second orientation adjustable mirrored elements.

12. A compensator/retarder system as in claim 10 which further comprises means for causing said compensator/retarder system to rotate during use about the propagation direction locus of said input beam of electromagnetic radiation.

13. A method of calibrating a spectroscopic rotating compensator material system investigation system comprising the steps of:

a. providing a present invention spectroscopic rotating compensator material system investigation system comprising:

a source of electromagnetic radiation;

a polarizer;

a compensator/retarder system comprising, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a stage for supporting a material system;
an analyzer system; and
a detector system;

b. developing a mathematical model of said spectroscopic rotating compensator material system investigation system which comprises as calibration parameter variables polarizer azimuthal angle orientation, present material system PSI, present material system DELTA, compensator azimuthal angle orientation(s), matrix components of said compensator/retarder system, analyzer azimuthal angle orientation, and optionally detector element image persistence and Readout non-idealities, which mathematical model is effectively a transfer function which enables calculation of electromagnetic beam intensity as a function of wavelength detected by a detector element, given intensity as a function of wavelength provided by said source of a polychromatic beam of electromagnetic radiation, said mathematical model optionally providing equations for coefficients of terms in said transfer function, said coefficients of terms being functions of calibration parameters;

c. causing a polychromatic beam of electromagnetic radiation produced by said source of a polychromatic beam of electromagnetic radiation, to pass through said polarizer, interact with a material system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through said compensator/retarder system positioned at a location selected from the group consisting of: before said stage for supporting a material system and after said stage for supporting a material system and both before and after said stage for supporting a sample system;

d. obtaining an at least two dimensional data set of intensity values vs. wavelength and a parameter selected from the group consisting of: angle-of-Incidence of said polychromatic beam of electromagnetic radiation with respect to a present material system, and azimuthal angle rotation of one element selected from the group consisting of: said polarizer and said analyzer, over time, while said compensator/retarder system is caused to continuously rotate and, optionally, from said data set calculating numerical values for coefficients of terms in the transfer function for said spectroscopic rotating compensator material system investigation system;

e. performing a mathematical regression of said mathematical model onto said at least two dimensional data set and/or onto values for coefficients of terms in the transfer function to evaluate said calibration parameters;

said regression based calibration procedure evaluated calibration parameters serving to compensate said mathematical model for non-achromatic characteristics and non-idealities of said compensator/retarder system, and for azimuthal angle orientations of said polarizer, analyzer and compensator/retarder system.

* * * * *